US008501215B2

(12) United States Patent
Chen et al.

(10) Patent No.: US 8,501,215 B2
(45) Date of Patent: *Aug. 6, 2013

(54) INJECTABLE MULTIMODAL POLYMER DEPOT COMPOSITIONS AND USES THEREOF

(76) Inventors: Guohua Chen, Sunnyvale, CA (US); Paul Houston, Hayward, CA (US); Lothar Kleiner, Los Altos, CA (US); Jeremy Wright, Los Altos, CA (US)

( * ) Notice: Subject to any disclaimer, the term of this patent is extended or adjusted under 35 U.S.C. 154(b) by 1391 days.

This patent is subject to a terminal disclaimer.

(21) Appl. No.: 10/628,984

(22) Filed: Jul. 28, 2003

(65) Prior Publication Data

US 2004/0022859 A1    Feb. 5, 2004

Related U.S. Application Data

(60) Provisional application No. 60/399,832, filed on Jul. 31, 2002.

(51) Int. Cl.
*A61F 2/00* (2006.01)
*A61F 13/00* (2006.01)
*A61K 9/14* (2006.01)

(52) U.S. Cl.
USPC .......................... 424/426; 424/422; 424/487

(58) Field of Classification Search
None
See application file for complete search history.

(56) References Cited

U.S. PATENT DOCUMENTS

| | | | |
|---|---|---|---|
| 3,797,492 A | 3/1974 | Place | 128/260 |
| 3,923,939 A | 12/1975 | Baker et al. | 264/49 |
| 3,987,790 A | 10/1976 | Eckenhoff et al. | 128/260 |
| 4,008,719 A | 2/1977 | Theeuwes et al. | 128/260 |
| 4,443,340 A | 4/1984 | May et al. | 210/697 |
| 4,568,559 A | 2/1986 | Nuwayser et al. | 427/3 |
| 4,623,588 A | 11/1986 | Nuwayser et al. | 428/402.24 |
| 4,668,506 A | 5/1987 | Bawa | 424/429 |
| 4,708,861 A | 11/1987 | Popescu et al. | 424/1.1 |
| 4,711,782 A | 12/1987 | Okada et al. | 424/455 |
| 4,713,244 A | 12/1987 | Bawa et al. | 424/429 |
| 4,853,218 A | 8/1989 | Yim et al. | 424/85.7 |
| 4,865,845 A | 9/1989 | Eckenhoff et al. | 424/424 |
| 4,866,050 A | 9/1989 | Ben-Amoz | 514/179 |
| 4,931,279 A | 6/1990 | Bawa et al. | 424/427 |
| 4,938,763 A | 7/1990 | Dunn et al. | 604/891.1 |
| 4,985,404 A | 1/1991 | Mitchell et al. | 514/6 |
| 5,019,400 A | 5/1991 | Gombotz et al. | 424/497 |
| 5,057,318 A | 10/1991 | Magruder et al. | 424/438 |
| 5,059,423 A | 10/1991 | Magruder et al. | 424/438 |
| 5,061,492 A | 10/1991 | Okada et al. | 424/423 |
| 5,077,033 A | 12/1991 | Viegas et al. | 514/668 |
| 5,085,866 A | 2/1992 | Cowsar et al. | 424/481 |
| 5,112,614 A | 5/1992 | Magruder et al. | 424/422 |
| 5,137,727 A | 8/1992 | Eckenhoff et al. | 424/422 |
| 5,151,093 A | 9/1992 | Theeuwes et al. | 604/892.1 |
| 5,181,914 A | 1/1993 | Zook | 604/307 |
| 5,209,746 A | 5/1993 | Balaban et al. | 604/892.1 |
| 5,234,692 A | 8/1993 | Magruder et al. | 424/473 |
| 5,234,693 A | 8/1993 | Magruder et al. | 424/473 |
| 5,242,910 A | 9/1993 | Damanj | 514/152 |
| 5,252,318 A | 10/1993 | Joshi et al. | 424/78.04 |
| 5,278,201 A | 1/1994 | Dunn et al. | 523/133 |
| 5,279,608 A | 1/1994 | Cheikh | 604/892.1 |
| 5,300,295 A | 4/1994 | Viegas et al. | 424/427 |
| 5,308,348 A | 5/1994 | Balaban et al. | 644/891.1 |
| 5,310,865 A | 5/1994 | Enomoto et al. | 528/361 |
| 5,324,519 A | 6/1994 | Dunn et al. | 424/426 |
| 5,330,452 A | 7/1994 | Zook | 604/307 |
| 5,336,057 A | 8/1994 | Fukuda et al. | 417/395 |
| 5,340,614 A | 8/1994 | Perman et al. | 427/2.24 |
| 5,342,627 A | 8/1994 | Chopra et al. | 424/473 |
| 5,415,866 A | 5/1995 | Zook | 424/448 |
| 5,441,732 A | 8/1995 | Hoeg et al. | 424/78.04 |
| 5,447,725 A | 9/1995 | Damani et al. | 424/435 |
| 5,456,679 A | 10/1995 | Balaban et al. | 604/892.1 |
| 5,487,897 A | 1/1996 | Polson et al. | 424/426 |
| 5,540,912 A | 7/1996 | Roorda et al. | 424/422 |
| 5,540,937 A * | 7/1996 | Billot et al. | 424/489 |
| 5,543,156 A | 8/1996 | Roorda et al. | 424/484 |
| 5,556,905 A | 9/1996 | Frappier et al. | 524/311 |
| 5,567,431 A | 10/1996 | Vert et al. | |
| 5,571,525 A | 11/1996 | Roorda et al. | 424/426 |
| 5,587,175 A | 12/1996 | Viegas et al. | 424/427 |
| 5,599,534 A | 2/1997 | Himmelstein et al. | 424/78.04 |

(Continued)

FOREIGN PATENT DOCUMENTS

| | | |
|---|---|---|
| JP | 08-501064 | 2/1996 |
| JP | 2000-511161 | 2/1996 |

(Continued)

OTHER PUBLICATIONS

Answers.com [online] gel retrieved from the Internet http://www.answers.com/topic/gel on Feb. 21, 2007 p. 1 of 1.*
Penco et al. Polymer International 1998, 46, 203-216.*
Le Corre et al. (International Journal of Pharmaceutics 1994, 107, 41-49).*
Bodmeier eta l. (International Journal of Pharmaceutics 1989, 51, 1-8).*
Blanco, M. D. et al. "Bupivacaine-loaded comatrix formed by alumin microspheres included in a poly(lactide-coglycolide) film: in vivo biocompatibility and drug release studies," *Biomaterials*, vol. 20, pp. 1919-1924, 1999.
Duenas, E. et al. "Sustained Delivery of rhVEGF from a Novel Injectable Liquid, Plad" *Proceed. Int'l. Symp. Control. Rel. Bioact. Mater.*, vol. 28, 2001.
Guevello, P. Le at al. "High-performance liquid chromatographic determination of buplvacain in plasma samples for biopharmaveutical studies and application to seven other local anaesthetics," *Journal of Chromatography*, vol 622, pp. 284-290, (1993).

(Continued)

*Primary Examiner* — Ernst Arnold

(57) ABSTRACT

Injectable depot compositions are provided that include a polymer matrix having a plurality of bioerodible, biocompatible polymers wherein each polymer of the plurality of polymers has a specified average molecular weight, and the polymer matrix has a broad molecular weight distribution of the plurality of polymers; a solvent having a miscibility in water of less than or equal to 7 wt % at 25° C., in an amount effective to plasticize the polymer and form a gel therewith; and a beneficial agent. The compositions have substantially improved shear thinning behavior and reduced injection force, rendering the compositions readily implanted beneath a patient's body surface by injection.

44 Claims, 13 Drawing Sheets

U.S. PATENT DOCUMENTS

| | | | |
|---|---|---|---|
| 5,599,552 A | 2/1997 | Dunn et al. | 424/423 |
| 5,610,184 A | 3/1997 | Shahinian, Jr. | 514/540 |
| 5,618,563 A | 4/1997 | Berde et al. | 424/501 |
| 5,620,700 A | 4/1997 | Berggren et al. | 424/435 |
| 5,651,986 A | 7/1997 | Brem et al. | 424/484 |
| 5,654,010 A | 8/1997 | Johnson et al. | 424/502 |
| 5,656,297 A | 8/1997 | Bernstein et al. | 424/484 |
| 5,660,817 A | 8/1997 | Masterman et al. | 424/49 |
| 5,674,292 A | 10/1997 | Tucker et al. | 623/16 |
| 5,681,873 A | 10/1997 | Norton et al. | 523/115 |
| 5,700,485 A | 12/1997 | Berde et al. | 424/501 |
| 5,707,644 A | 1/1998 | Illum | 424/434 |
| 5,708,011 A | 1/1998 | Bardsley et al. | 514/330 |
| 5,733,950 A | 3/1998 | Dunn et al. | 523/113 |
| 5,744,153 A | 4/1998 | Yewey et al. | 424/426 |
| 5,747,058 A | 5/1998 | Tipton et al. | 424/337 |
| 5,747,060 A | 5/1998 | Sackler et al. | 424/426 |
| 5,759,563 A | 6/1998 | Yewey et al. | 424/426 |
| 5,760,077 A | 6/1998 | Shahinian, Jr. | 514/540 |
| 5,766,637 A | 6/1998 | Shine et al. | 424/497 |
| 5,780,044 A | 7/1998 | Yewey et al. | 424/426 |
| 5,783,205 A | 7/1998 | Berggren et al. | 424/426 |
| 5,804,212 A | 9/1998 | Illum | 424/434 |
| 5,849,763 A | 12/1998 | Bardsley et al. | 514/445 |
| 5,910,502 A | 6/1999 | Gennery | 514/330 |
| 5,919,835 A | 7/1999 | Domb et al. | 523/113 |
| 5,922,340 A | 7/1999 | Berde et al. | 424/426 |
| 5,942,241 A | 8/1999 | Chasin et al. | 424/426 |
| 5,955,479 A | 9/1999 | Bardsley et al. | 514/330 |
| 5,958,443 A | 9/1999 | Viegas et al. | 424/427 |
| 5,972,326 A | 10/1999 | Galin et al. | 424/78.04 |
| 5,972,366 A | 10/1999 | Haynes et al. | 424/422 |
| 5,990,194 A | 11/1999 | Dunn et al. | 523/113 |
| 6,004,295 A | 12/1999 | Langer et al. | 604/164 |
| 6,046,187 A | 4/2000 | Berde et al. | 514/179 |
| 6,050,986 A | 4/2000 | Hektner | 604/508 |
| 6,086,909 A | 7/2000 | Harrison et al. | 424/430 |
| 6,103,266 A | 8/2000 | Tapolsky et al. | 424/484 |
| 6,106,301 A | 8/2000 | Merril | 434/262 |
| 6,117,425 A | 9/2000 | MacPhee et al. | 424/94.64 |
| 6,120,789 A | 9/2000 | Dunn | 424/426 |
| 6,120,804 A | 9/2000 | Drizen et al. | 424/488 |
| 6,129,933 A | 10/2000 | Oshlack et al. | 424/495 |
| 6,130,200 A | 10/2000 | Brodbeck et al. | 514/2 |
| 6,136,334 A | 10/2000 | Viegas et al. | 424/427 |
| 6,143,314 A | 11/2000 | Chandrashekar et al. | 424/426 |
| 6,193,991 B1 | 2/2001 | Shukla | 424/426 |
| 6,193,994 B1 | 2/2001 | Lee et al. | 424/444 |
| 6,197,327 B1 | 3/2001 | Harrison et al. | 424/430 |
| 6,214,387 B1 | 4/2001 | Berde et al. | 424/501 |
| 6,217,911 B1 | 4/2001 | Vaung et al. | 424/501 |
| 6,238,702 B1 | 5/2001 | Berde et al. | 424/489 |
| 6,248,345 B1 | 6/2001 | Goldenheim et al. | 424/426 |
| 6,255,502 B1 | 7/2001 | Penkler et al. | 552/549 |
| 6,261,547 B1 | 7/2001 | Bawa et al. | 424/78.04 |
| 6,309,375 B1 | 10/2001 | Glines et al. | 604/187 |
| 6,322,548 B1 | 11/2001 | Payne et al. | 604/500 |
| 6,331,311 B1 | 12/2001 | Brodbeck et al. | |
| 6,352,667 B1 | 3/2002 | English | 264/328.17 |
| 6,355,273 B1 | 3/2002 | Carli et al. | 424/489 |
| 6,372,245 B1 | 4/2002 | Bowman et al. | 424/427 |
| 6,375,659 B1 | 4/2002 | Erbe et al. | 606/94 |
| 6,395,293 B2 | 5/2002 | Polson et al. | 424/426 |
| 6,403,057 B1 | 6/2002 | Schneider et al. | 424/9.52 |
| 6,417,201 B1 | 7/2002 | Bardsley et al. | 514/330 |
| 6,423,818 B1 | 7/2002 | Matsuda et al. | 528/354 |
| 6,426,339 B1 | 7/2002 | Berde et al. | 514/180 |
| 6,432,415 B1 | 8/2002 | Osborne et al. | 424/400 |
| 6,451,346 B1 | 9/2002 | Shah | 424/486 |
| 6,534,081 B2 | 3/2003 | Goldenheim et al. | 424/426 |
| 6,759,431 B2 | 7/2004 | Hunter | |
| 2001/0004644 A1 | 6/2001 | Levin | 514/646 |
| 2001/0037104 A1 | 11/2001 | Zhang et al. | 604/502 |
| 2001/0046518 A1 | 11/2001 | Sawhney | 424/486 |
| 2001/0055607 A1 | 12/2001 | Levin | 424/435 |
| 2002/0001608 A1 | 1/2002 | Polson et al. | 424/426 |
| 2002/0004063 A1 | 1/2002 | Zhang | 424/443 |
| 2002/0010150 A1 | 1/2002 | Cortese et al. | 514/54 |
| 2002/0015712 A1 | 2/2002 | Mcbride et al. | 424/400 |
| 2002/0016338 A1 | 2/2002 | Mather et al. | 514/317 |
| 2002/0028181 A1 | 3/2002 | Miller et al. | 424/43 |
| 2002/0028243 A1 | 3/2002 | Masters | 424/484 |
| 2002/0037358 A1 | 3/2002 | Barry et al. | 427/2.1 |
| 2002/0039594 A1 | 4/2002 | Unger | 424/426 |
| 2002/0045668 A1 | 4/2002 | Dang et al. | 514/649 |
| 2002/0054915 A1 | 5/2002 | Goldenheim et al. | 424/497 |
| 2002/0061326 A1 | 5/2002 | Li et al. | 424/424 |
| 2002/0086971 A1 | 7/2002 | Pham | 528/354 |
| 2003/0027833 A1* | 2/2003 | Cleary et al. | 514/270 |
| 2003/0170289 A1 | 9/2003 | Chen et al. | |
| 2004/0001889 A1 | 1/2004 | Chen et al. | |
| 2004/0151753 A1 | 8/2004 | Chen et al. | |
| 2005/0079202 A1 | 4/2005 | Chen et al. | |
| 2007/0184084 A1 | 8/2007 | Chen et al. | |

FOREIGN PATENT DOCUMENTS

| | | |
|---|---|---|
| JP | 2000-5111161 | 2/1996 |
| JP | 2001-509146 | 7/2001 |
| WO | WO 93/24150 | 12/1993 |
| WO | WO 95/13799 | 5/1995 |
| WO | WO 98/27962 | 7/1998 |
| WO | WO 98/27963 | 7/1998 |
| WO | WO 99/47073 | 9/1999 |
| WO | WO 00/74650 A2 | 12/2000 |
| WO | 02/00137 | 1/2002 |
| WO | WO 02/38185 * | 5/2002 |
| WO | WO 02/45689 A1 | 6/2002 |
| WO | WO 02/058670 A1 | 8/2002 |
| WO | WO 02/067991 A1 | 9/2002 |
| WO | WO 03/041684 A2 | 5/2003 |
| WO | WO 03/041685 A1 | 5/2003 |
| WO | WO 03/041757 A2 | 5/2003 |

OTHER PUBLICATIONS

Garry, M. G. et al. "Evaluation of the efficency of a bioerodible bupivacaine polymer system on antinociception and inflammatory mediator release," *Pain*, vol. 82, pp. 49-55, 1999.

Lambert, W. J. at al. "Development of an in situ forming bidegradable poly-lactide—co-glycolide system for controlled release of proteins," *Journal of Controlled Release*, vol. 33, pp. 189-195 (1995).

Okumu, F. W. et al. "Sustained Delivery of Growth Hormone from a Novel Injectable Liquid, Plad," *Proceed. Int'l. Symp. Control. Rel. Bioact. Mater.*, vol. 28, 2001.

Okumu, F. W. et al. "Evaluation of Sabre™ Delivery System for Sustained Release of Growth Hormone—Formulation Design and In Vivo Assessment," *Proceed. Int'l. Symp. Control. Rel. Bioact. Mater.*, vol. 28, 2001.

Philip, B. K. et al. "The Economoc Impact of Opiods on Postoperative Pain Management," *Journal of Clinical Anesthesia*, vol. 14, pp. 354-364, 2002.

Jain, Rajeev A., "The manufacturing techniques of various drug loaded biodegradable poly(lactide-co-glycolide) (PLGA) devices," Biomaterials 21: 2475-2490 (2002).

Rivivarapu et al, "Polymer and microsphere blending to alter the release of a peptide from PLGA microspheres," European Journal of Pharmaceutics and Biopharmaceutics 50: 263-270 (2002).

International Search Report, dated Feb. 9, 2004 (4 pages).

Cleland, J. L. "Injectable Gels for Local and Systemic Delivery of Proteins," *Proceed. Int'l. Symp. Control. Rel. Bioact. Mater.*, vol. 28, 2001.

U.S. Appl. No. 60/336,254, filed Nov. 14, 2001, entitled "Injectable Depot Composition," inventor Chen et al. (total of 43 pages).

U.S. Appl. No. 60/336,307, filed Nov. 14, 2001, entitled "Injectable Depot Compositions and Uses Thereof," inventor Chen et al. (total of 51 pages).

Jain, Rajeev A., "The manufacturing techniques of various drug loaded biodegradable poly(lactide-co-glycolide) (PLGA) devices," Biomaterials 21: 2475-2490 (2000).

Ravivarapu et al., "Polymer and microsphere blending to alter the release of a peptide from PLGA microspheres," European Journal of Pharmaceutics and Biopharmaceutics 50: 263-270 (2000), Feb. 27, 2008.

Jarr, Em et al., "Sustained Release of Lidocaine from an Injectable Implant System for Treatment of Post-Operative Pain," *Proc. Int'l. Symp. Control. Rel. Bioact. Mater.*, 28 (1999) Controlled Release Society, Inc.

Penco et al., *Polymer International*, 1998, 46, 203-216.

English translation of Office Action, dated Jan. 22, 2010, from Japanese Application No. 2004-524891, which is a family member of the present application.

* cited by examiner

GPC diagrams of PLGAs with different MW distribution (a. uni-modal; b. multi-modal; c. bi-modal)

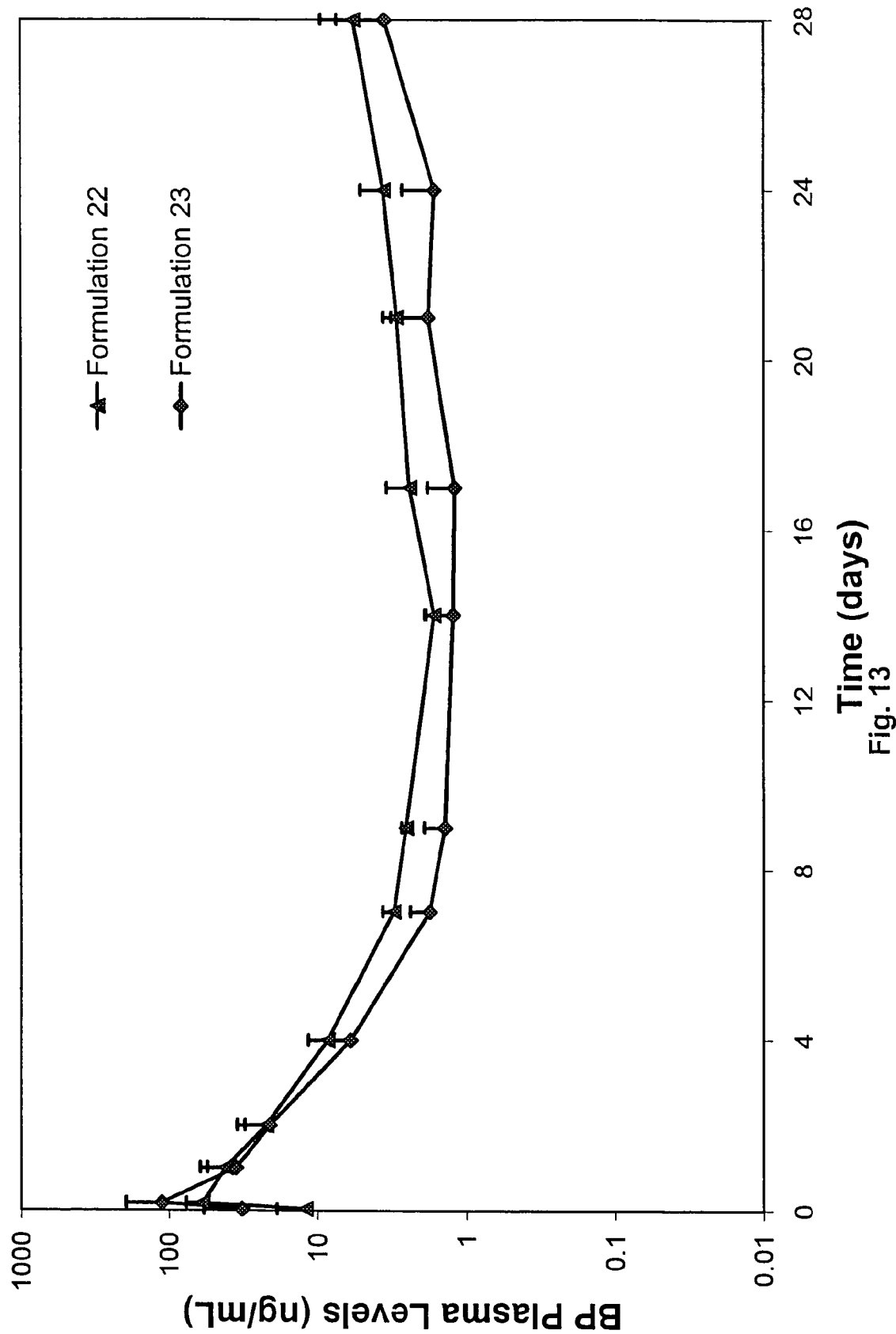

INJECTABLE MULTIMODAL POLYMER DEPOT COMPOSITIONS AND USES THEREOF

CROSS-REFERENCE TO RELATED APPLICATION

This application claims the benefit of U.S. Provisional Application No. 60/399,832, filed on Jul. 31, 2002.

BACKGROUND OF THE INVENTION

1. Field of the Invention

The present invention relates generally to a depot composition that can be injected into a desired location within a patient's body to form an implant, which provides for controlled, sustained release of a beneficial agent. More particularly, the present invention pertains to depot compositions of a beneficial agent and a polymer matrix, the polymer matrix having a plurality of bioerodible, biocompatible polymers wherein each polymer of the plurality of polymers has a specified average molecular weight; and the polymer matrix has a broad molecular weight distribution, preferably a multimodal distribution, of the plurality of polymers. The polymer matrix promotes shear thinning and improved injectability of the depot composition. The present invention also relates to a method of using the depot composition to administer a beneficial agent to a patient.

2. Related Art

Biodegradable polymers have been used for many years in medical applications. Illustrative devices composed of the biodegradable polymers include sutures, surgical clips, staples, implants, and drug delivery systems. The majority of these biodegradable polymers have been based upon glycolide, lactide, caprolactone, and copolymers thereof.

The biodegradable polymers can be thermoplastic materials, meaning that they can be heated and formed into various shapes, such as fibers, clips, staples, pins, films, etc. Alternatively, they can be thermosetting materials formed by cross-linking reactions, which lead to high-molecular-weight materials that do not melt or form flowable liquids at high temperatures. Although thermoplastic and thermosetting biodegradable polymers have many useful biomedical applications, there are several important limitations to their use in the bodies of various animals including humans, animals, birds, fish, and reptiles.

Solid implant drug delivery systems containing a drug incorporated in thermoplastic or thermosetting biodegradable polymers have been widely used successfully. Such implants have to be inserted into the body through an incision which is sometimes larger than desired by the medical profession and occasionally lead to a reluctance of the patients to accept such an implant or drug delivery system. The following U.S. Pat. Nos. 5,456,679; 5,336,057; 5,308,348; 5,279,608; 5,234,693; 5,234,692; 5,209,746; 5,151,093; 5,137,727; 5,112,614; 5,085,866; 5,059,423; 5,057,318; 4,865,845; 4,008,719; 3,987,790 and 3,797,492 are believed to be representative of such drug delivery systems and are incorporated herein by reference. These patents disclose reservoir devices, osmotic delivery devices, and pulsatile delivery devices for delivering beneficial agents.

Injecting drug delivery systems as small particles, microspheres, or microcapsules avoids the incision needed to implant drug delivery systems. However, these materials do not always satisfy the demand for a biodegradable implant. These materials are particulate in nature, do not form a continuous film or solid implant with the structural integrity needed for certain prostheses, the particles tend to aggregate and thus their behavior is hard to predict. When inserted into certain body cavities, such as a mouth, a periodontal pocket, the eye, or the vagina, where there is considerable fluid flow, these small particles, microspheres, or microcapsules are poorly retained because of their small size and discontinuous nature. Further, if there are complications, removal of microcapsule or small-particle systems from the body without extensive surgical intervention is considerably more difficult than with solid implants. Additionally, manufacture, storage and injectability of microspheres or microcapsules prepared from these polymers and containing drugs for release into the body present problems.

The art has developed various drug delivery systems in response to the aforementioned challenges. The following U.S. Pat. Nos. 5,990,194; 5,780,044; 5,733,950; 5,620,700; 5,599,552; 5,556,905 5,278,201; 5,242,910 and 4,938,763; and PCT publication WO 98/27962 are believed to be representative and are incorporated herein by reference. These patents disclose polymer compositions for injectable implants using solvents and/or plasticizers.

Previously described polymer formulations for injectable implants have used solvent/plasticizers that are very or relatively soluble in aqueous body fluids to promote rapid solidification of the polymer at the implant site and promote diffusion of drug from the implant. Rapid migration of water into such polymeric implants utilizing water soluble polymer solvents when the implants are placed in the body and exposed to aqueous body fluids, presents a serious problem. The rapid water uptake often results in implants having pore structures that are nonhomogeneous in size and shape. Typically, the surface pores take on a finger-like pore structure extending for as much as one-third of a millimeter or more from the implant surface into the implant, and such finger-like pores are open at the surface of the implant to the environment of use. The internal pores tend to be smaller and less accessible to the fluids present in the environment of use. The rapid water uptake characteristic often results in uncontrolled release of beneficial agent that is manifested by an initial, rapid release of beneficial agent from the polymer formulation, corresponding to a "burst" of beneficial agent being released from the implant. The burst often results in a substantial portion of the beneficial agent, if not all, being released in a very short time, e.g., hours or one to two days. Such an effect can be unacceptable, particularly in those circumstances where a controlled delivery is desired, i.e., delivery of beneficial agent in a controlled manner over a period of greater than two weeks or up to a month, or where there is a narrow therapeutic window and release of excess beneficial agent can result in adverse consequences to the subject being treated, or where it is necessary to mimic the naturally occurring daily profile of beneficial agents, such as hormones and the like, in the body of the subject being treated.

Accordingly, when such devices are implanted, the finger-like pores allow very rapid uptake of aqueous body fluids into the interior of the implant with consequent immediate and rapid dissolution of significant quantities of beneficial agent and unimpeded diffusion of beneficial agent into the environment of use, producing the burst effect discussed above.

Furthermore, rapid water uptake can result in premature polymer precipitation such that a hardened implant or one with a hardened skin is produced. The inner pores and much of the interior of the polymer containing beneficial agent are shut off from contact with the body fluids and a significant reduction in the release of beneficial agent can result over a not insignificant period of time ("lag time"). That lag time is undesirable from the standpoint of presenting a controlled, sustained release of beneficial agent to the subject being treated. What one observes, then, is a burst of beneficial agent being released in a short time period immediately after implantation, a lag time in which no or very little beneficial agent is being released, and subsequently continued delivery of beneficial agent (assuming beneficial agent remains after the burst) until the supply of beneficial agent is exhausted.

Various approaches to control burst and modulate and stabilize the delivery of the beneficial agent have been described. The following U.S. Pat. Nos. 6,130,200; 5,990,194; 5,780,044; 5,733,950; 5,656,297; 5,654,010; 4,985,404 and 4,853,218 and PCT publication WO 98/27962 are believed to be representative and are incorporated herein by reference. Notwithstanding some success, those methods have not been entirely satisfactory for the large number of beneficial agents that would be effectively delivered by implants.

An additional problem encountered with prior solvent-based depot formulations is that the viscosity of the injectable formulation is relatively high, particularly when higher molecular weight polymers are used, and the injection force needed to introduce the formulation into a patient's body is therefore high as well (see, e.g., U.S. Pat. No. 6,130,200). However, the high viscosity of the gel is desirable to maintain the integrity of the depot after injection and during the dispensing period and also to facilitate desired suspension characteristics of the beneficial agent in the gel.

To address this problem, those working in the field have employed various methods to reduce overall viscosity of the formulation, such as the use of lower molecular weight polymers, a lower polymer to solvent ratio, and agents that provide viscosity reduction. See, for example, U.S. Pat. Nos. 5,733,950, 5,780,044, and 5,990,194 to Dunn et al. International application WO 98/27962 and co-pending, co-owned U.S. provisional applications, Ser. Nos. 60/336,254 and 60/336,307, describe the formation of a thixotropic gel formulation that provides for shear thinning and more acceptable injectability of the gel, such that lower injection forces are needed to expel the gel from a syringe and also lower the likelihood of substantial discomfort to a subject by use of smaller needles than would otherwise be required.

Notwithstanding some success, the previously described systems have not been entirely satisfactory. For example, these approaches can result in drug particle settling; a higher initial release burst; relatively large amounts of emulsifying agent, e.g., about one-third of the total weight of the formulation; manufacturing problems related to solvent volatility; denaturation of proteins and peptide drugs depending on the solvent/emulsifying agent used, and the like. Additionally, the requirement that the bioerodible polymer have a low molecular weight is quite restrictive from a manufacturing standpoint.

It has been discovered that in certain systems, depot compositions with a polymer matrix, having a plurality of bioerodible, biocompatible polymers wherein each polymer of the plurality of polymers has a specified average molecular weight; the polymer matrix having a broad molecular weight distribution of the plurality of polymers (e.g., a multimodal distribution of high, medium and low molecular weight polymers), dissolved in a suitable polymer solvent results in depot compositions exhibiting substantially significantly improved shear thinning and further reduced injection force as compared to previously described depot gel formulations. The depot compositions exhibit non-Newtonian flow, i.e., shear thinning at a lower shear rate as compared to previously disclosed depot formulations having a narrower range of molecular weight distribution (e.g., unimodal distribution of medium molecular weight polymers), thus resulting in depot compositions that are readily injectable through needles having a gauge that when used is not unduly uncomfortable to a subject.

SUMMARY OF THE INVENTION

The present invention is directed to the aforementioned needs in the art, and provides an injectable depot composition that exhibits improved shear thinning behavior and thereby enables further reduced injection force and use of a small diameter (e.g., 16-gauge and higher) needle. In particular, the injectable depot composition increases the shear thinning behavior and composition homogeneity of the depot composition, without resulting in settling of the beneficial agent. The composition provides sustained release of a beneficial agent while limiting any initial burst effect, and offers increased composition flexibility with regard to the polymer/solvent ratio and the molecular weight of the bioerodible polymer. The depot compositions of the present invention reduce the injection force significantly without compromising the in vivo release profile of the beneficial agent.

In one aspect, then, the invention is directed to an injectable depot composition comprising:

(a) a polymer matrix comprising a plurality of bioerodible, biocompatible polymers wherein each polymer of the plurality of polymers has a specified average molecular weight; the polymer matrix having a broad molecular weight distribution of the plurality of polymers;

(b) a solvent having a miscibility in water of less than or equal to 7% at 25° C., in an amount effective to plasticize the polymer and form a gel therewith; and (c) a beneficial agent dissolved or dispersed in the gel. In a preferred embodiment, the polymer matrix has a multimodal molecular weight distribution of the plurality of bioerodible, biocompatible polymers; wherein a first of the plurality of polymers is a low molecular weight (LMW) polymer; a second of the plurality of polymers is a high molecular weight (HMW) polymer; and optionally a third of the plurality of polymers is a medium molecular weight (MMW) polymer. Preferably the polymer matrix has a polydispersity equal to or greater than 2; and preferably equal to or greater than 2.5.

In another aspect, the invention is directed to an injectable depot composition comprising:

(a) a polymer matrix comprising a plurality of bioerodible, biocompatible polymers; wherein a first of the plurality of polymers is a low molecular weight (LMW) polymer; and a second of the plurality of polymers is a high molecular weight (HMW) polymer; the polymer matrix having a bimodal molecular weight distribution of the plurality of polymers;

(b) a solvent having a miscibility in water of less than or equal to 7% at 25° C., in an amount effective to plasticize the polymer and form a gel therewith, wherein the solvent is an aromatic alcohol; and (c) a beneficial agent dissolved or dispersed in the gel.

In another aspect, the invention is directed to an injectable depot composition comprising:

(a) a polymer matrix comprising a plurality of bioerodible, biocompatible polymers; wherein a first of the plurality of polymers is a low molecular weight (LMW) polymer; a second of the plurality of polymers is a high molecular weight (HMW) polymer; a third of the plurality of polymers is a medium molecular weight (MMW) polymer; the polymer matrix having a broad, multimodal molecular weight distribution of the plurality of polymers;

(b) a solvent having a miscibility in water of less than or equal to 7% at 25° C., in an amount effective to plasticize the polymer and form a gel therewith, wherein the solvent is an aromatic alcohol; and (c) a beneficial agent dissolved or dispersed in the gel.

In another aspect the invention is directed to an injectable depot composition comprising:

(a) a polymer matrix comprising a plurality of bioerodible, biocompatible polymers; wherein a first of the plurality of polymers is a low molecular weight (LMW) polymer; and a second of the plurality of polymers is a high molecular weight (HMW) polymer; the polymer matrix having a bimodal molecular weight distribution of the plurality of polymers;

(b) an aromatic alcohol having a miscibility in water of less than or equal to 7% at 25° C., in an amount effective to plasticize the polymer and form a gel therewith, wherein the aromatic alcohol has the structural formula (I)

$$\text{Ar-(L)}_n\text{-OH} \qquad (I)$$

in which Ar is a substituted or unsubstituted aryl or heteroaryl group, n is zero or 1, and L is a linking moiety; and (c) a beneficial agent dissolved or dispersed in the gel.

In another aspect, the invention is directed to an injectable depot composition comprising:

(a) a polymer matrix comprising a plurality of bioerodible, biocompatible polymers; wherein a first of the plurality of polymers is a low molecular weight (LMW) polymer; a second of the plurality of polymers is a high molecular weight (HMW) polymer; a third of the plurality of polymers is a medium molecular weight (MMW) polymer; the polymer matrix having a broad, multimodal molecular weight distribution of the plurality of polymers;

(b) an aromatic alcohol having a miscibility in water of less than or equal to 7% at 25° C., in an amount effective to plasticize the polymer and form a gel therewith, wherein the aromatic alcohol has the structural formula (I)

$$\text{Ar-(L)}_n\text{-OH} \qquad (I)$$

in which Ar is a substituted or unsubstituted aryl or heteroaryl group, n is zero or 1, and L is a linking moiety; and (c) a beneficial agent dissolved or dispersed in the gel.

In another aspect, the invention is directed to an injectable depot composition comprising:

(a) a polymer matrix comprising a plurality of bioerodible, biocompatible polymers; wherein a first of the plurality of polymers is a low molecular weight (LMW) polymer; and a second of the plurality of polymers is a high molecular weight (HMW) polymer; the polymer matrix having a bimodal molecular weight distribution of the plurality of polymers;

(b) a solvent having a miscibility in water of less than or equal to 7% at 25° C., in an amount effective to plasticize the polymer and form a gel therewith, wherein the solvent is selected from the group consisting of esters of aromatic acids, aromatic ketones, and mixtures thereof; and (c) a beneficial agent dissolved or dispersed in the gel.

In another aspect, the invention is directed to an injectable depot composition comprising:

(a) a polymer matrix comprising a plurality of bioerodible, biocompatible polymers; wherein a first of the plurality of polymers is a low molecular weight (LMW) polymer; a second of the plurality of polymers is a high molecular weight (HMW) polymer; a third of the plurality of polymers is a medium molecular weight (MMW) polymer; the polymer matrix having a broad, multimodal molecular weight distribution of the plurality of polymers;

(b) a solvent having a miscibility in water of less than or equal to 7% at 25° C., in an amount effective to plasticize the polymer and form a gel therewith, wherein the solvent is selected from the group consisting of esters of aromatic acids, aromatic ketones, and mixtures thereof; and (c) a beneficial agent dissolved or dispersed in the gel.

In another aspect, the invention is directed to an injectable depot composition comprising:

(a) a polymer matrix comprising a plurality of bioerodible, biocompatible polymers; wherein a first of the plurality of polymers is a low molecular weight (LMW) polymer; and a second of the plurality of polymers is a high molecular weight (HMW) polymer; the polymer matrix having a bimodal molecular weight distribution of the plurality of polymers;

(b) a solvent selected from the group consisting of aromatic alcohols, esters of aromatic acids, aromatic ketones, and mixtures thereof, the solvent having a miscibility in water of less than or equal to 7% at 25° C., and present in an amount effective to plasticize the polymer and form a gel therewith; and (c) a beneficial agent dissolved or dispersed in the gel.

In another aspect, the invention is directed to an injectable depot composition comprising:

(a) a polymer matrix comprising a plurality of bioerodible, biocompatible polymers; wherein a first of the plurality of polymers is a low molecular weight (LMW) polymer; a second of the plurality of polymers is a high molecular weight (HMW) polymer; a third of the plurality of polymers is a medium molecular weight (MMW) polymer; the polymer matrix having a broad, multimodal molecular weight distribution of the plurality of polymers;

(b) a solvent selected from the group consisting of aromatic alcohols, esters of aromatic acids, aromatic ketones, and mixtures thereof, the solvent having a miscibility in water of less than or equal to 7% at 25° C., and present in an amount effective to plasticize the polymer and form a gel therewith; and (c) a beneficial agent dissolved or dispersed in the gel.

In one aspect, then, the invention is directed to an injectable depot composition comprising:

(a) a polymer matrix comprising a plurality of bioerodible, biocompatible polymers wherein each polymer of the plurality of polymers has a specified weight average molecular weight; the polymer matrix having a broad molecular weight distribution of the plurality of polymers;

(b) a solvent having a miscibility in water of less than or equal to 7% at 25° C., in an amount effective to plasticize the polymer and form a gel therewith; and (c) a beneficial agent dissolved or dispersed in the gel; wherein the depot composition has a reduced injection force as compared to a depot composition with a bioerodible, biocompatible polymer having a unimodal/narrower molecular weight distribution.

In another aspect, the invention comprises a method of administering, locally or systemically, a beneficial agent to a subject which comprises implanting beneath the subject's body surface a composition containing the beneficial agent; a polymer matrix comprising a plurality of bioerodible, biocompatible polymers wherein each polymer of the plurality of polymers has a specified average molecular weight; the polymer matrix having a broad molecular weight distribution of the plurality of polymers; wherein a first of the plurality of polymers is a low molecular weight (LMW) polymer; a second of the plurality of polymers is a high molecular weight (HMW) polymer; and optionally a third of the plurality of polymers is a medium molecular weight (MMW) polymer; and a solvent selected from the group consisting of aromatic alcohols, esters of aromatic acids, aromatic ketones, and mixtures thereof, the solvent having a miscibility in water of less than or equal to 7% at 25° C., and present in an amount effective to plasticize the polymer and form a gel therewith.

In another aspect, the invention comprises a method of administering, locally or systemically, a beneficial agent to a subject which comprises implanting beneath the subject's body surface a composition containing the beneficial agent; a polymer matrix comprising a plurality of bioerodible, biocompatible polymers wherein each polymer of the plurality of polymers has a specified average molecular weight; the polymer matrix having a broad molecular weight distribution of the plurality of polymers; wherein a first of the plurality of polymers is a low molecular weight (LMW) polymer; a second of the plurality of polymers is a high molecular weight (HMW) polymer; and optionally a third of the plurality of polymers is a medium molecular weight (MMW) polymer; and a solvent selected from the group consisting of aromatic alcohols, esters of aromatic acids, aromatic ketones, and mixtures thereof, the solvent having a miscibility in water of less than or equal to 7% at 25° C., and present in an amount effective to plasticize the polymer and form a gel therewith.

In preferred embodiments, the polymer matrix comprises a plurality of bioerodible, biocompatible polymers wherein each polymer of the plurality of polymers has a specified average molecular weight; the polymer matrix having a broad molecular weight distribution of the plurality of polymers; wherein a first of the plurality of polymers is a low molecular weight (LMW) polymer having an average molecular weight of about 3,000 to about 10,000; a second of the plurality of polymers is a high molecular weight (HMW) polymer having an average molecular weight of about 30,000 to about 250,000; and optionally a third of the plurality of polymers is a medium molecular weight (MMW) polymer having an average molecular weight of between about 10,000 to about 30,000.

Preferably, the polymer matrix comprises about 0 wt % to about 95 wt % of low molecular weight (LMW) polymer, preferably about 20 wt % to about 90 wt % of low molecular weight (LMW) polymer, more preferably about 30 wt % to about 80 wt % of low molecular weight (LMW) polymer, and more preferably about 40 wt % to about 75 wt % of low molecular weight (LMW) polymer; about 0 wt % to about 95 wt % of high molecular weight (HMW) polymer, preferably about 0 wt % to about 70 wt % of high molecular weight (HMW) polymer, preferably about 0 wt % to about 50 wt % of high molecular weight (HMW) polymer, preferably about 5 wt % to about 40 wt % of high molecular weight (HMW) polymer, more preferably about 10 wt % to about 30 wt % of high molecular weight (HMW) polymer, and more preferably about 15 wt % to about 25 wt % of high molecular weight (HMW) polymer; and about 0 wt % to about 95 wt % of medium molecular weight (MMW) polymer, preferably about 20 wt % to about 90 wt % of medium molecular weight (MMW) polymer, more preferably about 30 wt % to about 80 wt % of medium molecular weight (MMW) polymer, and more preferably about 40 wt % to about 60 wt % of medium molecular weight (MMW) polymer.

In preferred embodiments, the polymers include, but are not limited to, polylactides, polyglycolides, polycaprolactones, polyanhydrides, polyamines, polyurethanes, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, chitin, chitosan, hyaluronic acid and copolymers, terpolymers and mixtures thereof; more preferably, the polymers are polylactides, that is, a lactic acid-based polymer that can be based solely on lactic acid or can be a copolymer based on lactic acid and glycolic acid, and which may include small amounts of other comonomers that do not substantially affect the advantageous results that can be achieved in accordance with the present invention.

Preferably, the solvent is selected from the group consisting of an aromatic alcohol, an ester of an aromatic acid, and mixtures thereof. Preferably the system releases 40% or less by weight of the beneficial agent present in the viscous gel within the first 24 hours after implantation in the subject. More preferably, 30% or less by weight of the beneficial agent will be released within the first 24 hours after implantation, and the implanted composition has a burst index of twelve or less, preferably eight or less.

BRIEF DESCRIPTION OF THE DRAWINGS

The foregoing and other objects, features and advantages of the present invention will be more readily understood upon reading the following detailed description in conjunction with the drawings in which:

FIG. 13 is a graph illustrating the in vivo release profile of bupivacaine hydrochloride obtained from depot compositions present in this invention (formulations 22 and 23).

DETAILED DESCRIPTION OF THE INVENTION

Overview and Definitions

Figure 1:
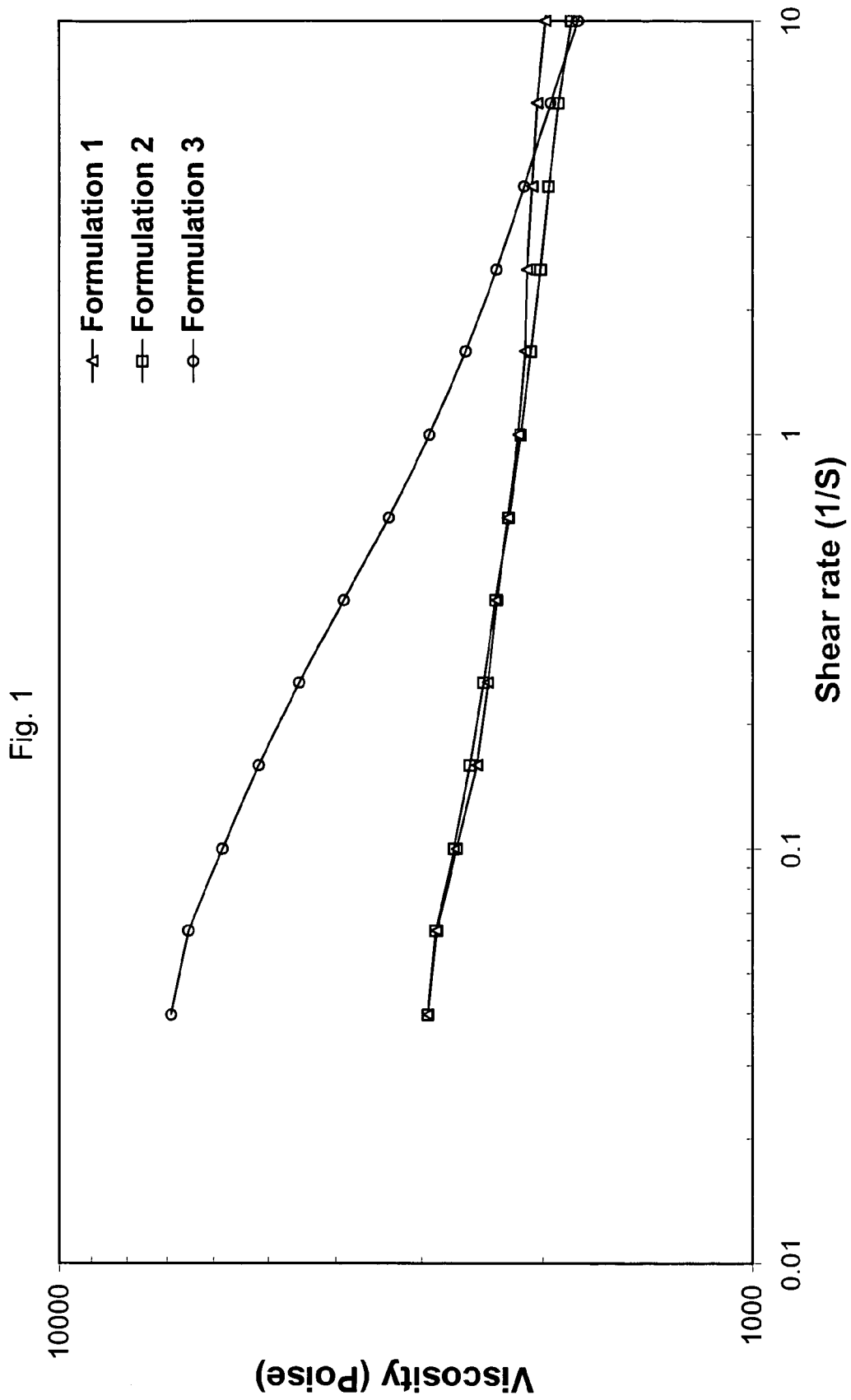
FIG. 1 is a graph illustrating the rheological behavior of depot gel compositions present in this invention (formulations 1 through 3).

The present invention is directed to an injectable depot composition that serves as an implanted sustained release beneficial agent delivery system after injection into a patient's body. In particular, the present invention pertains to an injectable depot composition that exhibits improved shear thinning behavior and a low injection force. The present invention also relates to a method of using the injectable depot composition to administer a beneficial agent to a patient.

The injectable depot composition is a gel formed from a polymer matrix comprising a plurality of bioerodible, biocompatible polymers wherein each polymer of the plurality of polymers has a specified average molecular weight; the polymer matrix having a broad molecular weight distribution of the plurality of polymers; a solvent having a miscibility in water of less than or equal to 7% at 25° C.; and a beneficial agent. In a preferred embodiment, the polymer matrix has a multimodal molecular weight distribution of the plurality of polymers; wherein a first of the plurality of polymers is a low molecular weight (LMW) polymer; a second of the plurality of polymers is a high molecular weight (HMW) polymer; and optionally a third of the plurality of polymers is a medium molecular weight (MMW) polymer. In additional embodiments, the polymer matrix has a bimodal molecular weight distribution of the plurality of polymers, the plurality polymers being selected from a low molecular weight (LMW) polymer, a high molecular weight (HMW) polymer, and a medium molecular weight (MMW) polymer.

In some embodiments, pore formers and solubility modulators of the beneficial agent may be added to the implant systems to provide desired release profiles from the implant systems, along with typical pharmaceutical excipients and other additives that do not change the beneficial aspects of the present invention.

Previously described depot gel formulations having a narrower range of molecular weight distribution, generally a unimodal molecular weight distribution, exhibit a Newtonian flow. These formulations are highly viscous and maintain their viscosity at high shear, thus making it difficult to inject these formulations. It has been discovered that a depot gel composition having a broader range of molecular weight distribution, as described herein, exhibits a non-Newtonian flow (shear thinning) at a lower shear rate than the previously described depot gel formulations. In particular, when these depot gel compositions are subjected to a high shear, such as during injection, the viscosity of the composition decreases considerably, resulting in improved injectability. Further, these depot gel compositions promote shear thinning behavior, and significantly decrease injection force without affecting the controlled, sustained release rate of the beneficial agent, and without the undesirable burst effect. As described in greater detail herein, the injection force is reduced approximately 30% to 40% as compared to the previously described depot compositions (see e.g., Examples 11 and 13 through 18, and FIGS. 1 and 3 through 12, as described in greater detail hereinafter).

The composition provides sustained release of the beneficial agent by restricting water migration from the aqueous environment surrounding the implant system, thus delivering the beneficial agent over a prolonged period of time. Water uptake is controlled by virtue of the water-immiscible solvents. Because the polymer of the composition is bioerodible, the implant system does not have to be surgically removed after beneficial agent is depleted from the implant.

Generally, the compositions of the invention are gel-like and form a substantially homogeneous nonporous structure throughout the implant upon implantation and during drug delivery, even as it hardens. Furthermore, while the polymer gel implant will slowly harden when subjected to an aqueous environment, the hardened implant may maintain a rubbery (nonrigid) composition with the glass transition temperature $T_g$ being below 37° C.

Additionally, the high molecular weight (HMW) polymers within the polymer matrix of the depot composition generally harden faster when the solvent exits the depot, potentially accelerating the formation of a beneficial agent-diffusion barrier. Thus depot gel compositions provide a controlled, sustained release of the beneficial agent from the depot composition, without the undesirable burst effect.

The preferred compositions herein allow beneficial agent to be loaded into the interior of the polymer at levels that are above that required to saturate the beneficial agent in water, thereby facilitating zero order release of beneficial agent. Additionally, the preferred compositions may provide viscous gels that have a glass transition temperature that is less than 37° C., such that the gel remains nonrigid for a period of time after implantation of 24 hours or more.

In describing and claiming the present invention, the following terminology will be used in accordance with the definitions set out below.

The singular forms "a," "an," and "the" include plural referents unless the context clearly dictates otherwise. Thus, for example, reference to "a solvent" includes a single solvent as well as a mixture of two or more different solvents, reference to "a beneficial agent" includes a single beneficial agent as well as two or more different beneficial agents in combination, reference to "an aromatic alcohol" includes a single aromatic alcohol as well as a mixture of two or more different aromatic alcohols, and the like.

The term "beneficial agent" means an agent that effects a desired beneficial, often pharmacological, effect upon administration to a human or an animal, whether alone or in combination with other pharmaceutical excipients or inert ingredients.

As used herein, the term "polynucleotide" refers to a polymeric form of nucleotides of any length, either ribonucleotides or deoxyribonucleotides, and includes double- and single-stranded DNA and RNA. It also includes known types of modifications, substitutions, and internucleotide modifications, which are known in the art.

As used herein, the term "recombinant polynucleotide" refers to a polynucleotide of genomic, cDNA, semisynthetic, or synthetic origin which, by virtue of its origin or manipulation: is not associated with all or a portion of a polynucleotide with which it is associated in nature; is linked to a polynucleotide other than that to which it is linked in nature; or does not occur in nature.

As used herein, the term "polypeptide" refers to a polymer of amino acids, including, for example, peptides, oligopeptides, and proteins and derivatives, analogs and fragments thereof, as well as other modifications known in the art, both naturally occurring and non-naturally occurring.

As used herein, the term "purified" and "isolated" when referring to a polypeptide or nucleotide sequence means that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present.

The term "AUC" means the area under the curve obtained from an in vivo assay in a subject by plotting blood plasma concentration of the beneficial agent in the subject against time, as measured from the time of implantation of the composition, to a time "t" after implantation. The time t will correspond to the delivery period of beneficial agent to a subject.

The term "burst index" means, with respect to a particular composition intended for systemic delivery of a beneficial agent, the quotient formed by dividing (i) the AUC calculated for the first time period after implantation of the composition into a subject divided by the number of hours in the first time period ($t_1$), by (ii) the AUC calculated for the time period of delivery of beneficial agent, divided by the number of hours in the total duration of the delivery period ($t_2$). For example the burst index at 24 hours is the quotient formed by dividing (i) the AUC calculated for the first 24 hours after implantation of the composition into a subject divided by the number 24, by (ii) the AUC calculated for the time period of delivery of beneficial agent, divided by the number of hours in the total duration of the delivery period.

The phrase "dissolved or dispersed" is intended to encompass all means of establishing a presence of beneficial agent in the gel composition and includes dissolution, dispersion, suspension and the like.

The term "systemic" means, with respect to delivery or administration of a beneficial agent to a subject, that the beneficial agent is detectable at a biologically significant level in the blood plasma of the subject.

The term "local" means, with respect to delivery or administration of a beneficial agent to a subject, that the beneficial agent is delivered to a localized site in the subject but is not detectable at a biologically significant level in the blood plasma of the subject.

The term "gel vehicle" means the composition formed by mixture of the polymer and solvent in the absence of the beneficial agent.

The term "prolonged period" means a period of time over which release of a beneficial agent from the implant of the invention occurs, which will generally be about one week or longer, and preferably about 30 days or longer.

The term "initial burst" means, with respect to a particular composition of this invention, the quotient obtained by dividing (i) the amount by weight of beneficial agent released from the composition in a predetermined initial period of time after implantation, by (ii) the total amount of beneficial agent that is to be delivered from an implanted composition. It is understood that the initial burst may vary depending on the shape and surface area of the implant. Accordingly, the percentages and burst indices associated with initial burst described herein are intended to apply to compositions tested in a form resulting from dispensing of the composition from a standard syringe.

The term "solubility modulator" means, with respect to the beneficial agent, an agent that will alter the solubility of the beneficial agent, with reference to polymer solvent or water, from the solubility of beneficial agent in the absence of the modulator. The modulator may enhance or retard the solubility of the beneficial agent in the solvent or water. However, in the case of beneficial agents that are highly water soluble, the solubility modulator will generally be an agent that will retard the solubility of the beneficial agent in water. The effects of solubility modulators of the beneficial agent may result from interaction of the solubility modulator with the solvent, or with the beneficial agent itself, such as by the formation of complexes, or with both. For the purposes hereof, when the solubility modulator is "associated" with the beneficial agent, all such interactions or formations as may occur are intended. Solubility modulators may be mixed with the beneficial agent prior to its combination with the viscous gel or may be added to the viscous gel prior to the addition of the beneficial agent, as appropriate.

The terms "subject" and "patient" mean, with respect to the administration of a composition of the invention, an animal or a human being.

Since all solvents, at least on a molecular level, will be soluble in water (i.e., miscible with water) to some very limited extent, the term "immiscible" as used herein means that 7% or less by weight, preferably 5% or less, of the solvent is soluble in or miscible with water. For the purposes of this disclosure, solubility values of solvent in water are considered to be determined at 25° C. Since it is generally recognized that solubility values as reported may not always be conducted at the same conditions, solubility limits recited herein as percent by weight miscible or soluble with water as part of a range or upper limit may not be absolute. For example, if the upper limit on solvent solubility in water is recited herein as "7% by weight," and no further limitations on the solvent are provided, the solvent "triacetin," which has a reported solubility in water of 7.17 grams in 100 ml of water, is considered to be included within the limit of 7%. A solubility limit in water of less than 7% by weight as used herein does not include the solvent triacetin or solvents having solubilities in water equal to or greater than triacetin.

The term "bioerodible" refers to a material that gradually decomposes, dissolves, hydrolyzes and/or erodes in situ. Generally, the "bioerodible" polymers herein are polymers that are hydrolyzable, and bioerode in situ primarily through hydrolysis.

The term "polydispersity" refers to the quotient ($M_w/M_n$) of average molecular weight ($M_w$) divided by the number average molecular weight ($M_n$).

The term "broad molecular weight distribution" refers to a polymer composition of a plurality of polymers, the polymer composition having a polydispersity greater than 2, preferably equal to or greater than 2.5.

The term "narrow molecular weight distribution" refers to a polymer composition having a polydispersity index less than 2.

As used herein, the term "multimodal polymer matrix" refers to polymer matrix of a plurality of polymers, the matrix having a multimodal distribution of molecular masses, wherein each polymer within the polymer matrix may have a broad or narrow molecular weight distribution. Generally, a multimodal polymer matrix has more than one peak on a molecular weight distribution plot (frequency on the abscissa and molecular weight on the ordinate) (see, e.g., FIG. 2). For example, multimodal polymer matrix comprises a plurality of polymers, such as HMW PLGA RG503, MMW RG502 and LMW PLGA, and has a molecular weight distribution ($M_w/M_n$) of 2.34.

The term "bimodal polymer matrix" refers to a polymer matrix of a plurality of polymers, the matrix having a bimodal distribution of molecular masses, wherein each polymer within the polymer matrix may have a broad or narrow molecular weight distribution. Generally, a bimodal polymer matrix has two peaks on a molecular weight distribution plot (frequency on the abscissa and molecular weight on the ordinate) (see, e.g., FIG. 2). For example, a bimodal polymer matrix comprises a plurality of polymers, such as HMW PLGA RG503 with LMW PLGA, and has a molecular weight distribution ($M_w/M_n$) of 2.75.

The terms "a single modal polymer matrix" and "a unimodal polymer matrix" are used interchangeably and refer to a polymer matrix having a unimodal and narrow distribution of molecular masses. Generally, a unimodal polymer matrix has a single peak on a molecular weight distribution plot (frequency on the abscissa and molecular weight on the ordinate) (see, e.g., FIG. 2). For example, unimodal polymer matrix comprises a polymer, such as MMW PLGA RG502, and has a molecular weight distribution ($M_w/M_n$) of 1.90.

The term "low molecular weight (LMW) polymer" refers to biocompatible, bioerodible polymers having an average molecular weight ranging from about 3000 to about 10,000; preferably from about 3000 to about 9000; more preferably from about 4000 to about 8000; and more preferably, the low molecular weight polymer has a molecular weight of about 7000, about 6000, about 5000, about 4000 and about 3000 as determined by gel permeation chromatography (GPC).

The term "medium molecular weight (MMW) polymer" refers to biocompatible, bioerodible polymers having an average molecular weight ranging from between about 10,000 to about 30,000; preferably from about 12,000 to about 20,000; more preferably from about 14,000 to about 18,000; and more preferably the medium molecular weight polymer has a molecular weight of about 14,000, about 15,000, about 16,000, about 17,000 and about 18,000 as determined by gel permeation chromatography (GPC). In preferred embodiments, an MMW polymer is PLGA RG502.

The term "high molecular weight (HMW) polymer" refers to biocompatible, bioerodible polymers having an average molecular weight of greater than 30,000; preferably from about 30,000 to about 250,000; more preferably from about 30,000 to about 120,000 as determined by gel permeation chromatography (GPC). In preferred embodiments, a HMW polymer is PLGA RG503.

The polymer, solvent and other agents of the invention must be "biocompatible"; that is they must not cause irritation or necrosis in the environment of use. The environment of use is a fluid environment and may comprise a subcutaneous, intramuscular, intravascular (high/low flow), intramyocardial, adventitial, intratumoral, or intracerebral portion, wound sites, tight joint spaces or body cavity of a human or animal.

The term "thixotropic" is used in its conventional sense to refer to a gel composition that can liquefy or at least exhibit a decrease in apparent viscosity upon application of mechanical force, such as shear force. The extent of the reduction is in part a function of the shear rate of the gel when subjected to the shearing force. When the shearing force is removed, the viscosity of the thixotropic gel returns to a viscosity at or near that which it displayed prior to being subjected to the shearing force. Accordingly, a thixotropic gel may be subjected to a shearing force when injected from a syringe which temporarily reduces its viscosity during the injection process. When the injection process is completed, the shearing force is removed and the gel returns very near to its previous state.

A "thixotropic agent" as used herein is one that increases the thixotropy of the composition in which it is contained, promoting shear thinning and enabling use of reduced injection force.

The following definitions apply to the molecular structures described herein:

As used herein, the phrase "having the formula" or "having the structure" is not intended to be limiting and is used in the same way that the term "comprising" is commonly used.

The term "alkyl" as used herein refers to a saturated hydrocarbon group typically although not necessarily containing 1 to about 30 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, preferably 1 to 4 carbon atoms. "Substituted alkyl" refers to an alkyl substituted with one or more substituent groups, and the terms "heteroatom-containing alkyl" and "heteroalkyl" refer to an alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl or lower alkyl.

The term "aryl" as used herein, and unless otherwise specified, refers to an aromatic substituent containing a single aromatic ring or multiple aromatic rings that are fused together, linked covalently, or linked to a common group, such as a methylene or ethylene moiety. Preferred aryl groups contain one aromatic ring or two fused or linked aromatic rings, e.g., phenyl, naphthyl, biphenyl, diphenylether, diphenylamine, benzophenone, and the like, and most preferred aryl groups are monocyclic. "Substituted aryl" refers to an aryl moiety substituted with one or more substituent groups, and the terms "heteroatom-containing aryl" and "heteroaryl" refer to an aryl in which at least one carbon atom is replaced with a heteroatom. Unless otherwise indicated, the term "aryl" includes heteroaryl, substituted aryl, and substituted heteroaryl groups.

The term "aralkyl" refers to an alkyl group substituted with an aryl group, wherein alkyl and aryl are as defined above. The term "heteroaralkyl" refers to an alkyl group substituted with a heteroaryl group. Unless otherwise indicated, the term "aralkyl" includes heteroaralkyl and substituted aralkyl groups as well as unsubstituted aralkyl groups. Generally, the term "aralkyl" herein refers to an aryl-substituted lower alkyl group, preferably a phenyl substituted lower alkyl group, such as benzyl, phenethyl, 1-phenylpropyl, 2-phenylpropyl, and the like.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heterocyclic" refers to a cyclic substituent that is heteroatom-containing, the term "heteroaryl" refers to an aryl substituent that is heteroatom-containing, and the like.

By "substituted" as in "substituted alkyl," "substituted aryl" and the like, as alluded to in some of the aforementioned definitions, is meant that in the alkyl or aryl moiety, respectively, at least one hydrogen atom bound to a carbon atom is replaced with one or more noninterfering substituents, such as hydroxyl, alkoxy, thio, amino, halo, and the like.

I. Injectable Depot Compositions:

As described previously, injectable depot compositions for delivery of beneficial agents over a prolonged period of time may be formed as viscous gels prior to injection of the depot into a subject. The viscous gel supports dispersed beneficial agent to provide appropriate delivery profiles, which include those having low initial burst, of the beneficial agent as the beneficial agent is released from the depot over time.

Typically, the viscous gel will be injected from a standard hypodermic syringe that has been prefilled with the beneficial agent-viscous gel composition to form the depot. It is often preferred that injections take place using the smallest size needle (i.e., smallest diameter) to reduce discomfort to the subject when the injection takes place through the skin and into subcutaneous tissue. It is desirable to be able to inject gels through needles ranging from 16 gauge and higher, preferably 20 gauge and higher, more preferably 22 gauge and higher, even more preferably 24 gauge and higher. With highly viscous gels, i.e., gels having a viscosity of about 200 poise or greater, injection forces to dispense the gel from a syringe having a needle in the 20 to 30 gauge range may be so high as to make the injection difficult or reasonably impossible when done manually. At the same time, the high viscosity of the gel is desirable to maintain the integrity of the depot after injection and during the dispensing period and also to facilitate desired suspension characteristics of the beneficial agent in the gel.

The depot gel composition described herein exhibits reduced viscosity when subjected to shear force. The extent of the reduction is in part a function of the shear rate of the gel when subjected to the shearing force, the molecular weight of the polymer and the polydispersity of the polymer matrix. When the shearing force is removed, the viscosity of the depot gel composition returns to a viscosity at or near that which it displayed prior to being subjected to the shearing force. Accordingly, the depot gel composition may be subjected to a shearing force when injected from a syringe which temporarily reduces its viscosity during the injection process. When the injection process is completed, the shearing force is removed and the gel returns very near to its previous state.

A. The Bioerodible, Biocompatible Polymer:

Polymers that are useful in conjunction with the methods and compositions of the invention are bioerodible, i.e., they gradually hydrolyze, dissolve, physically erode, or otherwise disintegrate within the aqueous fluids of a patient's body. Generally, the polymers bioerode as a result of hydrolysis or physical erosion, although the primary bioerosion process is typically hydrolysis.

Such polymers include, but are not limited to, polylactides, polyglycolides, polycaprolactones, polyanhydrides, polyamines, polyurethanes, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, chitin, chitosan, hyaluronic acid and copolymers, terpolymers and mixtures thereof.

Presently preferred polymers are polylactides, that is, a lactic acid-based polymer that can be based solely on lactic acid or can be a copolymer based on lactic acid and glycolic acid, and which may include small amounts of other comonomers that do not substantially affect the advantageous results that can be achieved in accordance with the present invention. As used herein, the term "lactic acid" includes the isomers L-lactic acid, D-lactic acid, DL-lactic acid and lactide, while the term "glycolic acid" includes glycolide. Most preferred are poly(lactide-co-glycolide)copolymers, commonly referred to as "PLGA." The polymer may have a monomer ratio of lactic acid/glycolic acid of from about 100:0 to about 15:85, preferably from about 75:25 to about 30:70, more preferably from about 60:40 to about 40:60, and an especially useful copolymer has a monomer ratio of lactic acid/glycolic acid of about 50:50.

In contrast to prior polymer-based injectable depots, the present invention allows use of a polymer matrix comprising a plurality of bioerodible, biocompatible polymers wherein each polymer of the plurality of polymers has a specified average molecular weight; the polymer matrix having a broad molecular weight distribution of the plurality of polymers. In preferred embodiments, the polymer matrix has a multimodal molecular weight distribution of a plurality of polymers; wherein a first of the plurality of polymers is a low molecular weight (LMW) polymer; a second of the plurality of polymers is a high molecular weight (HMW) polymer; and optionally a third of the plurality of polymers is a medium molecular weight (MMW) polymer; each polymer having a polydispersity of at least 2. Preferably, the polymer matrix comprises about 0 wt % to about 95 wt % of low molecular weight (LMW) polymer, preferably about 20 wt % to about 90 wt % of low molecular weight (LMW) polymer, more preferably about 30 wt % to about 80 wt % of low molecular weight (LMW) polymer, and more preferably about 40 wt % to about 75 wt % of low molecular weight (LMW) polymer; about 0 wt % to about 95 wt % of high molecular weight (HMW) polymer, preferably about 0 wt % to about 70 wt % of high molecular weight (HMW) polymer, preferably about 0 wt % to about 50 wt % of high molecular weight (HMW) polymer, preferably about 5 wt % to about 40 wt % of high molecular weight (HMW) polymer, more preferably about 10 wt % to about 30 wt % of high molecular weight (HMW) polymer, and more preferably about 15 wt % to about 25 wt % of high molecular weight (HMW) polymer; and about 0 wt % to about 95 wt % of medium molecular weight (MMW) polymer, preferably about 20 wt % to about 90 wt % of medium molecular weight (MMW) polymer, more preferably about 30 wt % to about 80 wt % of medium molecular weight (MMW) polymer, and more preferably about 40 wt % to about 60 wt % of medium molecular weight (MMW) polymer.

The low molecular weight (LMW) bioerodible polymers have an average molecular weight ranging from about 3000 to about 10,000; preferably from about 3000 to about 9000; more preferably from about 4000 to about 8000; and more preferably the low molecular weight polymer has a molecular weight of about 7000, about 6000, about 5000, about 4000 and about 3000 as determined by gel permeation chromatography (GPC).

The medium molecular weight (MMW) bioerodible polymers have an average molecular weight ranging from between about 10,000 to about 30,000; preferably from about 12,000 to about 20,000; more preferably from about 14,000 to about 18,000; and more preferably the medium molecular weight polymer has a molecular weight of about 14,000, about 15,000, about 16,000, about 17,000 and about 18,000 as determined by gel permeation chromatography (GPC). In preferred embodiments, an MMW polymer is PLGA RG502.

The high molecular weight (HMW) bioerodible polymers have an average molecular weight of greater than 30,000; preferably from about 30,000 to about 250,000; more preferably from about 30,000 to about 120,000 as determined by gel permeation chromatography (GPC). In preferred embodiments, a HMW polymer is PLGA RG503.

As indicated in aforementioned U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further comonomer) in accordance with the techniques set forth in U.S. Pat. No. 5,310,865. The contents of all of these patents are incorporated by reference. Suitable lactic acid-based polymers are available commercially. For instance, 50:50 lactic acid:glycolic acid copolymers having molecular weights of 8,000, 10,000, 30,000 and 100,000 are available from Boehringer Ingelheim (Petersburg, Va.), Medisorb Technologies International L.P. (Cincinatti, Ohio) and Birmingham Polymers, Inc. (Birmingham, Ala.) as described below.

Examples of polymers include, but are not limited to, Poly (D,L-lactide) Resomer® L104, PLA-L104, code no. 33007, Poly (D,L-lactide-co-glycolide) 50:50 Resomer® RG502, code 0000366, Poly (D,L-lactide-co-glycolide) 50:50 Resomer® RG502H, PLGA-502H, code no. 260187, Poly (D,L-lactide-co-glycolide) 50:50 Resomer® RG503, PLGA- 503, code no. 0080765, Poly (D,L-lactide-co-glycolide) 50:50 Resomer® RG506, PLGA-506, code no. 95051, Poly (D,L-lactide-co-glycolide) 50:50 Resomer® RG755, PLGA-755, code no. 95037, Poly L-Lactide MW 2,000 (Resomer® L 206, Resomer® L 207, Resomer® L 209, Resomer® L 214); Poly D,L Lactide (Resomer® R 104, Resomer® R 202, Resomer® R 203, Resomer® R 206, Resomer® R 207, Resomer® R 208); Poly L-Lactide-co-D,L-lactide 90:10 (Resomer® LR 209); Poly glycolide (Resomer® G 205); Poly D,L-lactide-co-glycolide 50:50 (Resomer® RG 504 H, Resomer® RG 504, Resomer® RG 505); Poly D-L-lactide-co-glycolide 75:25 (Resomer® RG 752, Resomer® RG 756); Poly D,L-lactide-co-glycolide 85:15 (Resomer® G 858); Poly L-lactide-co-trimethylene carbonate 70:30 (Resomer® LT 706); Poly dioxanone (Resomer® X 210) (Boehringer Ingelheim Chemicals, Inc., Petersburg, Va.).

Additional examples include, but are not limited to, DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinatti, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone Poly DL-lactide-co-caprolactone 25:75; and Poly DL-lactide-co-caprolactone 75:25 (Birmingham Polymers, Inc., Birmingham, Ala.).

The biocompatible bioerodible polymers are present in the gel composition in an amount ranging from about 5 to about 90% by weight, preferably from about 25 to about 80% by weight and typically from about 35 to about 75% by weight of the viscous gel, the viscous gel comprising the combined amounts of the biocompatible polymer and a solvent having a miscibility in water that is less than 7 wt % at 25° C. As discussed earlier, preferably, the polymer matrix comprises about 0 wt % to about 95 wt % of low molecular weight (LMW) polymer, preferably about 20 wt % to about 90 wt % of low molecular weight (LMW) polymer, more preferably about 30 wt % to about 80 wt % of low molecular weight (LMW) polymer, and more preferably about 40 wt % to about 75 wt % of low molecular weight (LMW) polymer; about 0 wt % to about 95 wt % of high molecular weight (HMW) polymer, preferably about 0 wt % to about 70 wt % of high molecular weight (HMW) polymer, preferably about 0 wt % to about 50 wt % of high molecular weight (HMW) polymer, preferably about 5 wt % to about 40 wt % of high molecular weight (HMW) polymer, more preferably about 10 wt % to about 30 wt % of high molecular weight (HMW) polymer, and more preferably about 15 wt % to about 25 wt % of high molecular weight (HMW) polymer; and about 0 wt % to about 95 wt % of medium molecular weight (MMW) polymer, preferably about 20 wt % to about 90 wt % of medium molecular weight (MMW) polymer, more preferably about 30 wt % to about 80 wt % of medium molecular weight (MMW) polymer, and more preferably about 40 wt % to about 60 wt % of medium molecular weight (MMW) polymer.

The solvent will be added to polymer in amounts described below, to provide implantable or injectable viscous gels. Again, the combination LMW, MMW and HMW and the solvent described herein enables a much wider range of polymer/solvent ratios than that obtainable previously, and provides a depot composition having improved injectability.

B. Solvents:

The injectable depot composition of the invention contains a water-immiscible solvent having a miscibility in water that is less than 7 wt % at 25° C., in addition to the bioerodible polymer, the thixotropic agent and the beneficial agent. The solvent must be biocompatible, should form a gel, preferably a viscous gel with the polymer, and restrict water uptake into the implant. Suitable solvents will substantially restrict the uptake of water by the implant and, as noted above, may be characterized as immiscible in water, i.e., having a solubility or miscibility in water of at most 7% by weight. Preferably, the water solubility of the aromatic alcohol is 5 wt % or less, more preferably 3 wt % or less, and even more preferably 1 wt % or less. Most preferably, the solubility of the aromatic alcohol in water is equal to or less than 0.5 wt %. In preferred embodiments, the solvent is selected from the group consisting of an aromatic alcohol, esters of aromatic acids, aromatic ketones, and mixtures thereof.

Water miscibility may be determined experimentally as follows: Water (1 to 5 g) is placed in a tared clear container at a controlled temperature, about 25° C., and weighed, and a candidate solvent is added dropwise. The solution is swirled to observe phase separation. When the saturation point appears to be reached, as determined by observation of phase separation, the solution is allowed to stand overnight and is re-checked the following day. If the solution is still saturated, as determined by observation of phase separation, then the percent (w/w) of solvent added is determined. Otherwise more solvent is added and the process repeated. Solubility or miscibility is determined by dividing the total weight of solvent added by the final weight of the solvent/water mixture. When solvent mixtures are used, they are premixed prior to adding to the water.

The aromatic alcohol has the structural formula (I)

$$\text{Ar-(L)}_n\text{-OH} \tag{I}$$

wherein Ar is a substituted or unsubstituted aryl or heteroaryl group, n is zero or 1, and L is a linking moiety. Preferably, Ar is a monocyclic aryl or heteroaryl group, optionally substituted with one or more noninterfering substituents, such as hydroxyl, alkoxy, thio, amino, halo, and the like. More preferably, Ar is an unsubstituted five- or six-membered aryl or heteroaryl group, such as phenyl, cyclopentadienyl, pyridinyl, pyrimadinyl, pyrazinyl, pyrrolyl, pyrazolyl, imidazolyl, furanyl, thiophenyl, thiazolyl, isothiazolyl, or the like. The subscript "n" is zero or 1, meaning that the linking moiety L may or may not be present. Preferably, n is 1 and L is generally a lower alkylene linkage, such as methylene or ethylene, wherein the linkage may include heteroatoms, such as O, N or S. Most preferably, Ar is phenyl, n is 1, and L is methylene, such that the aromatic alcohol is benzyl alcohol.

The aromatic acid ester or ketone must be biocompatible, should form a viscous gel with the polymer, and restrict water uptake into the implant. Like the aromatic alcohol, suitable aromatic acid esters and ketones will substantially restrict the uptake of water by the implant and, as noted above, may be characterized as immiscible in water, i.e., having a solubility or miscibility in water of at most 7% by weight. Preferably, the water solubility of the solvent alcohol is 5 wt % or less, more preferably 3 wt % or less, and even more preferably 1 wt % or less. Most preferably, the solubility of the solvent in water is equal to or less than 0.5 wt %.

The aromatic acid ester or ketone may be selected from the lower alkyl and aralkyl esters of aromatic acids, and aryl and aralkyl ketones. Generally, although not necessarily, the aromatic acid esters and ketones will respectively have the structural formula (II) or (III)

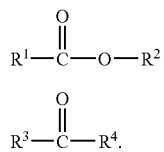

$$R^1-\overset{\overset{O}{\|}}{C}-O-R^2 \quad\quad (II)$$

$$R^3-\overset{\overset{O}{\|}}{C}-R^4. \quad\quad (III)$$

In the ester of formula (II), $R^1$ is substituted or unsubstituted aryl, aralkyl, heteroaryl or heteroaralkyl, preferably substituted or unsubstituted aryl or heteroaryl, more preferably monocyclic or bicyclic aryl or heteroaryl optionally substituted with one or more noninterfering substituents, such as hydroxyl, carboxyl, alkoxy, thio, amino, halo, and the like, still more preferably five- or six-membered aryl or heteroaryl, such as phenyl, cyclopentadienyl, pyridinyl, pyrimadinyl, pyrazinyl, pyrrolyl, pyrazolyl, imidazolyl, furanyl, thiophenyl, thiazolyl, or isothiazolyl, and most preferably five- or six-membered aryl. $R^2$ is hydrocarbyl or heteroatom-substituted hydrocarbyl, typically lower alkyl or substituted or unsubstituted aryl, aralkyl, heteroaryl or heteroaralkyl, preferably lower alkyl or substituted or unsubstituted aralkyl or heteroaralkyl, more preferably lower alkyl or monocyclic or bicyclic aralkyl or heteroaralkyl optionally substituted with one or more noninterfering substituents, such as hydroxyl, carboxyl, alkoxy, thio, amino, halo, and the like, still more preferably lower alkyl or five- or six-membered aralkyl or heteroaralkyl, and most preferably lower alkyl or five- or six-membered aryl optionally substituted with one or more additional ester groups having the structure —O—(CO)—$R^1$. Most preferred esters are benzoic acid and phthalic acid derivatives.

In the ketone of formula (III), $R^3$ and $R^4$ may be selected from any of the $R^1$ and $R^2$ groups identified above.

Art recognized benzoic acid derivatives from which solvents having the requisite solubility may be selected include, without limitation: 1,4-cyclohexane dimethanol dibenzoate, diethylene glycol dibenzoate, dipropylene glycol dibenzoate, polypropylene glycol dibenzoate, propylene glycol dibenzoate, diethylene glycol benzoate and dipropylene glycol benzoate blend, polyethylene glycol (200) dibenzoate, isodecyl benzoate, neopentyl glycol dibenzoate, glyceryl tribenzoate, pentaerylthritol tetrabenzoate, cumylphenyl benzoate, trimethyl pentanediol dibenzoate.

Art recognized phthalic acid derivatives from which solvents having the requisite solubility may be selected include: Alkyl benzyl phthalate, bis-cumyl-phenyl isophthalate, dibutoxyethyl phthalate, dimethyl phthalate, dimethyl phthalate, diethyl phthalate, dibutyl phthalate, diisobutyl phthalate, butyl octyl phthalate, diisoheptyl phthalate, butyl octyl phthalate, diisononyl phthalate, nonyl undecyl phthalate, dioctyl phthalate, di-isooctyl phthalate, dicapryl phthalate, mixed alcohol phthalate, di-(2-ethylhexyl) phthalate, linear heptyl, nonyl, phthalate, linear heptyl, nonyl, undecyl phthalate, linear nonyl phthalate, linear nonyl undecyl phthalate, linear dinonyl, didecyl phthalate (diisodecyl phthalate), diundecyl phthalate, ditridecyl phthalate, undecyldodecyl phthalate, decyltridecyl phthalate, blend (50/50) of dioctyl and didecyl phthalates, butyl benzyl phthalate, and dicyclohexyl phthalate.

Most preferred solvents are derivatives of benzoic acid and include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate and benzyl benzoate, with benzyl benzoate being most especially preferred.

The composition may also include, in addition to the water-immiscible solvent(s), one or more additional miscible solvents ("component solvents"), provided that any such additional solvent is other than a lower alkanol. Component solvents compatible and miscible with the primary solvent(s) may have a higher miscibility with water and the resulting mixtures may still exhibit significant restriction of water uptake into the implant. Such mixtures will be referred to as "component solvent mixtures." Useful component solvent mixtures may exhibit solubilities in water greater than the primary solvents themselves, typically between 0.1 weight percent and up to and including 50 weight percent, preferably up to and including 30 weight percent, and most preferably up to and including 10 weight percent, without detrimentally affecting the restriction of water uptake exhibited by the implants of the invention.

Component solvents useful in component solvent mixtures are those solvents that are miscible with the primary solvent or solvent mixture, and include, but are not limited, to triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, polyethylene glycol, octanol, ethyl lactate, propylene glycol, propylene carbonate, ethylene carbonate, butyrolactone, ethylene oxide, propylene oxide, N-methyl-2-Pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacyclo-heptan-2-one, and mixtures thereof.

The solvent or solvent mixture is capable of dissolving the polymer to form a viscous gel that can maintain particles of the beneficial agent dissolved or dispersed and isolated from the environment of use prior to release. The compositions of the present invention provide implants having a low burst index. Water uptake is controlled by the use of a solvent or component solvent mixture that solubilizes or plasticizes the polymer but substantially restricts uptake of water into the implant.

The solvent or solvent mixture is typically present in an amount of from about 95 to about 5% by weight, preferably about 75 to about 15% by weight, and most preferably about 65% to about 20% by weight of the viscous gel. In an especially preferred embodiment, the solvent is selected from an aromatic alcohol, lower alkyl and aralkyl esters of benzoic acid. Presently, the most preferred solvents are benzyl alcohol, benzyl benzoate and the lower alkyl esters of benzoic acid. In certain embodiments, the solvent comprises a mixture of the aromatic alcohol (formula I), aromatic acid ester (formula II) and ketone (formula III). Generally, the weight ratio of the aromatic alcohol to the ester or ketone is in the range of about 1% to about 99%, preferably in the range of about 10% to about 90%, often in the range of about 20% to about 80%.

The viscous gel formed by mixing the polymer and the solvent typically exhibits a viscosity of from about 200 to about 200,000 poise, preferably from about 2,000 to about 50,000 poise, often from about 1,000 to about 50,000 poise measured at a 0.1 sec⁻¹ shear rate and 25° C. using a Haake Rheometer at about one to two days after mixing is completed. Mixing the polymer with the solvent can be achieved with conventional low shear equipment, such as a Ross double planetary mixer, for from about ten minutes to about one hour, although shorter and longer periods may be chosen by one skilled in the art depending on the particular physical characteristics of the composition being prepared. Since it is often desirable to administer the implant as an injectable composition, a countervailing consideration when forming implants that are viscous gels is that the polymer, solvent and beneficial agent composition have sufficiently low viscosity in order to permit it to be forced through a small diameter, e.g., 16-gauge and higher, preferably 20-gauge and higher, more preferably 22-gauge and higher, even more preferably 24-gauge and higher gauge, needle. If necessary, adjustment of viscosity of the gel for injection can be accomplished with emulsifying agents as described herein. Yet, such compositions should have adequate dimensional stability so as to remain localized and be able to be removed if necessary. The particular gel or gel-like compositions of the present invention satisfy such requirements.

C. Beneficial Agents:

The beneficial agent can be any physiologically or pharmacologically active substance or substances optionally in combination with pharmaceutically acceptable carriers and additional ingredients, such as antioxidants, stabilizing agents, permeation enhancers, etc., that do not substantially adversely affect the advantageous results that can be attained by the present invention. The beneficial agent may be any of the agents which are known to be delivered to the body of a human or an animal and that are preferentially soluble in water rather than in the polymer-dissolving solvent. These agents include drug agents, medicaments, vitamins, nutrients, or the like. Included among the types of agents which meet this description are lower molecular weight compounds, proteins, peptides, genetic material, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, chemotherapeutic agents, immunosuppressive agents, anti-inflammatory agents including anti-inflammatory corticosteroids, antiproliferative agents, antimitotic agents, angiogenic agents, antipsychotic agents, central nervous system (CNS) agents, anticoagulants, fibrinolytic agents, growth factors, antibodies, ocular drugs, and metabolites, analogs (including synthetic and substituted analogs), derivatives (including aggregative conjugates/fusion with other macromolecules and covalent conjugates with unrelated chemical moieties by means known in the art) fragments, and purified, isolated, recombinant and chemically synthesized versions of these species.

Examples of drugs that may be delivered by the composition of the present invention include, but are not limited to, procaine, procaine hydrochloride, tetracaine, tetracaine hydrochloride, cocaine, cocaine hydrochloride, chloroprocaine, chloroprocaine hydrochloride, proparacaine, proparacaine hydrochloride, piperocaine, piperocaine hydrochloride, hexylcaine, hexylcaine hydrochloride, naepaine, naepaine hydrochloride, benzoxinate, benzoxinate hydrochloride, cyclomethylcaine, cyclomethylcaine hydrochloride, cyclomethylcaine sulfate, lidocaine, lidocaine hydrochloride, bupivicaine, bupivicaine hydrochloride, mepivicaine, mepivacaine hydrochloride, prilocaine, prilocaine hydrochloride, dibucaine and dibucaine hydrochloride, etidocaine, benzocaine, propoxycaine, dyclonin, pramoxine, oxybuprocaine, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofluorophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives, such as betamethasone, triamcinolone, methyltestosterone, 1 7-S-estradiol, ethinyl estradiol, ethinyl estradiol 3-methyl ether, prednisolone, 17α-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinopril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons, such as interferon alpha-2a, interferon alpha-2b, and consensus interferon, interleukins, growth factors, such as epidermal growth factors (EGF), platelet-derived growth factors (PDGF), fibroblast growth factors (FGF), transforming growth factors-α (TGF-α), transforming growth factors-β (TGF-β), erythropoietin (EPO), insulin-like growth factor-I (IGF-I), insulin-like growth factor-II (IGF-II), interleukin-1, interleukin-2, interleukin-6, interleukin-8, tumor necrosis factor-α (TNF-α), tumor necrosis factor-β (TNF-β), Interferon-α (INF-α), Interferon-β (INF-β), Interferon-γ (INF-γ), Interferon-ω (INF-ω), colony stimulating factors (CGF), vascular cell growth factor (VEGF), thrombopoietin (TPO), stromal cell-derived factors (SDF), placenta growth factor (PIGF), hepatocyte growth factor (HGF), granulocyte macrophage colony stimulating factor (GM-CSF), glial-derived neurotropin factor (GDNF), granulocyte colony stimulating factor (G-CSF), ciliary neurotropic factor (CNTF), bone morphogenic proteins (BMP), coagulation factors, human pancreas hormone releasing factor, analogs and derivatives of these compounds, and pharmaceutically acceptable salts of these compounds, or their analogs or derivatives.

Additional examples of drugs that may be delivered by the composition of the present invention include, but are not limited to, antiproliferative/antimitotic agents including natural products, such as vinca alkaloids (i.e., vinblastine, vincristine, and vinorelbine), paclitaxel, epidipodophyllotoxins (i.e., etoposide, teniposide), antibiotics (dactinomycin, actinomycin D, daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents, such as $G(GP)II_bIII_a$ inhibitors and vitronectin receptor antagonists; antiproliferative/antimitotic alkylating agents, such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazine (DTIC); antiproliferative/antimitotic antimetabolites, such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide hormones (i.e., estrogen); antipsychotic agents (such as antipsychotic drugs, neuroleptic drugs, tranquilizers and antipsychotic agents binding to dopamine, histamine, muscarinic cholinergic, adrenergic and serotonin receptors, including but not limited to phenothiazines, thioxanthenes, butyrophenones, dibenzoxazepines, dibenzodiazepines and diphenylbutylpiperidines) central nervous system (CNS) agents; anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory agents, such as adrenocortical steroids (cortisol, cortisone, fludrocortisone, prednisone, prednisolone, 6α-methylprednisolone, triamcinolone, betamethasone, and dexamethasone), nonsteroidal agents (salicylic acid derivatives, i.e., aspirin; para-aminophenol derivativies, i.e., acetominophen); indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blocker; nitric oxide donors; anti-sense oligonucleotides and combinations thereof; cell cycle inhibitors, mTOR inhibitors, and growth factor signal transduction kinase inhibitors, analogs and derivatives of these compounds, and pharmaceutically acceptable salts of these compounds, or their analogs or derivatives.

In certain preferred embodiments, the beneficial agent includes chemotactic growth factors, proliferative growth factors, stimulatory growth factors, and transformational peptide growth factors including genes, precursors, post-translational variants, metabolites, binding proteins, receptors, receptor agonists and antagonists of the following growth factor families: epidermal growth factors (EGFs), platelet-derived growth factor (PDGFs), insulin-like growth factors (IGFs), fibroblast-growth factors (FGFs), transforming-growth factors (TGFs), interleukins (ILs), colony-stimulating factors (CSFs, MCFs, GCSFs, GMCSFs), Interferons (IFNs), endothelial growth factors (VEGF, EGFs), erythropoietins (EPOs), angiopoietins (ANGs), placenta-derived growth factors (PIGFs), and hypoxia induced transcriptional regulators (HIFs).

The present invention also finds application with chemotherapeutic agents for the local application of such agents to avoid or minimize systemic side effects. Gels of the present invention containing chemotherapeutic agents may be injected directly into the tumor tissue for sustained delivery of the chemotherapeutic agent over time. In some cases, particularly after resection of the tumor, the gel may be implanted directly into the resulting cavity or may be applied to the remaining tissue as a coating. In cases in which the gel is implanted after surgery, it is possible to utilize gels having higher viscosities since they do not have to pass through a small diameter needle. Representative chemotherapeutic agents that may be delivered in accordance with the practice of the present invention include, for example, carboplatin, cisplatin, paclitaxel, BCNU, vincristine, camptothecin, etopside, cytokines, ribozymes, interferons, oligonucleotides and oligonucleotide sequences that inhibit translation or transcription of tumor genes, functional derivatives of the foregoing, and generally known chemotherapeutic agents such as those described in U.S. Pat. No. 5,651,986. The present application has particular utility in the sustained delivery of water soluble chemotherapeutic agents, such as, for example, cisplatin and carboplatin and the water soluble derivatives of paclitaxel. Those characteristics of the invention that minimize the burst effect are particularly advantageous in the administration of water soluble beneficial agents of all kinds, but particularly those compounds that are clinically useful and effective but may have adverse side effects.

To the extent not mentioned above, the beneficial agents described in aforementioned U.S. Pat. No. 5,242,910 can also be used. One particular advantage of the present invention is that materials, such as proteins, as exemplified by the enzyme lysozyme, and cDNA, and DNA incorporated into vectors both viral and nonviral, which are difficult to microencapsulate or process into microspheres can be incorporated into the compositions of the present invention without the level of degradation caused by exposure to high temperatures and denaturing solvents often present in other processing techniques.

The beneficial agent is preferably incorporated into the viscous gel formed from the polymer and the solvent in the form of particles typically having an average particle size of from about 0.1 to about 250 microns, preferably from about 1 to about 200 microns and often from 30 to 125 microns. For instance, particles having an average particle size of about 5 microns have been produced by spray drying or freeze drying an aqueous mixture containing 50% sucrose and 50% chicken lysozyme (on a dry weight basis) and mixtures of 10 to 20% hGH and 15 to 30 mM zinc acetate. Such particles have been used in certain of the examples illustrated in the figures. Conventional lyophilization processes can also be utilized to form particles of beneficial agents of varying sizes using appropriate freezing and drying cycles.

To form a suspension or dispersion of particles of the beneficial agent in the viscous gel formed from the polymer and the solvent, any conventional low shear device can be used, such as a Ross double planetary mixer, at ambient conditions. In this manner, efficient distribution of the beneficial agent can be achieved substantially without degrading the beneficial agent.

The beneficial agent is typically dissolved or dispersed in the composition in an amount of from about 0.1% to about 50% by weight, preferably in an amount of from about 1% to about 30%, more preferably in an amount of about 2% to about 20%, and often 2 to 10% by weight of the combined amounts of the polymer mixture, solvent, and beneficial agent. Depending on the amount of beneficial agent present in the composition, one can obtain different release profiles and burst indices. More specifically, for a given polymer and solvent, by adjusting the amounts of these components and the amount of the beneficial agent, one can obtain a release profile that depends more on the degradation of the polymer than the diffusion of the beneficial agent from the composition or vice versa. In this respect, at lower beneficial agent loading rates, one generally obtains a release profile reflecting degradation of the polymer wherein the release rate increases with time. At higher loading rates, one generally obtains a release profile caused by diffusion of the beneficial agent wherein the release rate decreases with time. At intermediate loading rates, one obtains combined release profiles so that if desired, a substantially constant release rate can be attained. In order to minimize burst, loading of beneficial agent on the order of 30% or less by weight of the overall gel composition, i.e., polymer, solvent and beneficial agent, is preferred, and loading of 20% or less is more preferred.

Release rates and loading of beneficial agent will be adjusted to provide for therapeutically effective delivery of the beneficial agent over the intended sustained delivery period. Preferably, the beneficial agent will be present in the polymer gel at concentrations that are above the saturation concentration of beneficial agent in water to provide a drug reservoir from which the beneficial agent is dispensed. While the release rate of beneficial agent depends on the particular circumstances, such as the beneficial agent to be administered, release rates on the order of from about 0.1 micrograms/day to about 10 milligrams/day, preferably from about 1 microgram/day to about 5 milligrams per day, more preferably from about 10 micrograms/day to about 1 milligram/day, for periods of from about 24 hours to about 180 days, preferably 24 hours to about 120 days, more preferably 24 hours to about 90 days, often three days to about 90 days can be obtained. Further, the dose of beneficial agent may be adjusted by adjusting the amount of depot gel injected. Greater amounts may be delivered if delivery is to occur over shorter periods. Generally, higher release rate is possible if a greater burst can be tolerated. In instances where the gel composition is surgically implanted, or used as a "leave behind" depot when surgery to treat the disease state or another condition is concurrently conducted, it is possible to provide higher doses that would normally be administered if the implant was injected. Further, the dose of beneficial agent may be controlled by adjusting the volume of the gel implanted or the injectable gel injected. Preferably, the system releases 40% or less by weight of the beneficial agent present in the viscous gel within the first 24 hours after implantation in the subject. More preferably, 30% or less by weight of the beneficial agent will be released within the first 24 hours after implantation, and the implanted composition has a burst index of twelve or less, preferably eight or less.

D. Optional Additional Components:

Other components may be present in the gel composition, to the extent they are desired or provide useful properties to the composition, such as polyethylene glycol, hydroscopic agents, stabilizing agents, pore-forming agents, thixotropic agents and others. When the composition includes a peptide or a protein that is soluble in or unstable in an aqueous environment, it may be highly desirable to include a solubility modulator that may, for example, be a stabilizing agent, in the composition. Various modulating agents are described in U.S. Pat. Nos. 5,654,010 and 5,656,297, the disclosures of which are incorporated herein by reference. In the case of hGH, for example, it is preferable to include an amount of a salt of a divalent metal, preferably zinc. Examples of such modulators and stabilizing agents, which may form complexes with the beneficial agent or associate to provide the stabilizing or modulated release effect, include metal cations, preferably divalent, present in the composition as magnesium carbonate, zinc carbonate, calcium carbonate, magnesium acetate, magnesium sulfate, zinc acetate, zinc sulfate, zinc chloride, magnesium chloride, magnesium oxide, magnesium hydroxide, other antacids, and the like. The amounts of such agents used will depend on the nature of the complex formed, if any, or the nature of the association between the beneficial agent and the agent. Molar ratios of solubility modulator or stabilizing agent to beneficial agent of about 100:1 to 1:1, preferably 10:1 to 1:1, typically can be utilized.

Pore-forming agents include biocompatible materials that when contacted with body fluids dissolve, disperse, or degrade to create pores or channels in the polymer matrix. Typically, organic and nonorganic materials that are water soluble, such as sugars (e.g., sucrose, dextrose), water soluble salts (e.g., sodium chloride, sodium phosphate, potassium chloride, and sodium carbonate), water soluble solvents, such as N-methyl-2-pyrrolidone and polyethylene glycol and water soluble polymers (e.g., carboxymethylcellulose, hydroxypropylcellulose, and the like), can conveniently be used as pore formers. Such materials may be present in amounts varying from about 0.1% to about 100% of the weight of the polymer, but will typically be less than 50% and more typically less than 10 to 20% of the weight of polymer.

Thixotropic agents include agents that impart thixotropic properties to the polymer gel, such as lower alkanols (e.g., ethanol, isopropanol), and the like. It is to be understood that the thixotropic agent of the present invention does not constitute a mere diluent or a polymer solvent that reduces viscosity by simply decreasing the concentration of the components of the composition. The use of conventional diluents can reduce viscosity, but can also cause the burst effect mentioned previously when the diluted composition is injected. In contrast, the injectable depot composition of the present invention can be formulated to avoid the burst effect by selecting the thixotropic agent so that once injected into place, the thixotropic agent has little impact on the release properties of the original system. Preferably, the system releases 40% or less by weight of the beneficial agent present in the viscous gel within the first 24 hours after implantation in the subject. More preferably, 30% or less by weight of the beneficial agent will be released within the first 24 hours after implantation, and the implanted composition has a burst index of twelve or less, preferably eight or less.

II. Utility and Administration:

The means of administration of the implants is not limited to injection, although that mode of delivery may often be preferred. Where the implant will be administered as a leave-behind product, it may be formed to fit into a body cavity existing after completion of surgery or it may be applied as a flowable gel by brushing or palleting the gel onto residual tissue or bone. Such applications may permit loading of beneficial agent in the gel above concentrations typically present with injectable compositions.

Compositions of this invention without beneficial agent are useful for wound healing, bone repair and other structural support purposes.

To further understand the various aspects of the present invention, the results set forth in the previously described figures were obtained in accordance with the following examples.

Example 1

Depot Gel Preparation

A gel vehicle for use in an injectable depot of the composition was prepared as follows. A glass vessel was tarred on a Mettler PJ3000 top loader balance. Poly (D,L-lactide-co-glycolide) (PLGA), (L/G ratio of 50/50) with an inherent viscosity of 0.15 (PLGA-BPI, Birmingham Polymers, Inc., Birmingham, Ala.), and Resomer® PLGA RG502 (L/G ratio of 50/50), or Resomer® PLGA RG503 (L/G ratio of 50/50), were weighed into the glass vessel. The glass vessel containing the polymer was tarred and the corresponding solvent was added. Amounts expressed as percentages for various polymer/solvent combinations are set forth in Table 1, below. The polymer/solvent mixture was stirred at 250±50 rpm (IKA electric stirrer, IKA-Werke GmbH & Co., Stanfen, Germany) for about five to ten minutes, resulting in a sticky paste-like substance containing polymer particles. The vessel containing the polymer/solvent mixture was sealed and placed in a temperature controlled incubator equilibrated to 37° C. for one to four days, with intermittent stirring, depending on solvent and polymer type and solvent and polymer ratios. The polymer/solvent mixture was removed from the incubator when it appeared to be a clear amber homogeneous solution. Thereafter, the mixture was placed in an oven (65° C.) for 30 minutes. It was noted that the PLGA was dissolved in the mixture upon removal from the oven.

Additional depot gel vehicles are prepared with the following solvents or mixtures of solvents: benzyl benzoate, benzyl alcohol, ethyl benzoate, and mixtures thereof and the following polymers: Poly (D,L-lactide) Resomer® L104, PLA-L104, code no. 33007, Poly (D,L-lactide-co-glycolide) 50:50 Resomer® RG502, code 0000366, Poly (D,L-lactide-co-glycolide) 50:50 Resomer® RG502H, PLGA-502H, code no. 260187, Poly (D,L-lactide-co-glycolide) 50:50 Resomer® RG503, PLGA-503, code no. 0080765, Poly (D,L-lactide-co-glycolide) 50:50 Resomer® RG755, PLGA-755, code no. 95037, Poly L-Lactide MW 2,000 (Resomer® L 206, Resomer® L 207, Resomer® L 209, Resomer® L 214); Poly D,L Lactide (Resomer® R 104, Resomer® R 202, Resomer® R 203, Resomer® R 206, Resomer® R 207, Resomer® R 208); Poly L-Lactide-co-D, L-lactide 90:10 (Resomer® LR 209); Poly D-L-lactide-co-glycolide 75:25 (Resomer® RG 752, Resomer® RG 756); Poly D,L-lactide-co-glycolide 85:15 (Resomer® RG 858); Poly L-lactide-co-trimethylene carbonate 70:30 (Resomer® LT 706); Poly dioxanone (Resomer® X 210) (Boehringer Ingelheim Chemicals, Inc., Petersburg, Va.); DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High; MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinatti, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone; Poly DL-lactide-co-caprolactone 25:75; and Poly DL-lactide-co-caprolactone 75:25 (Birmingham Polymers, Inc., Birmingham, Ala.).

TABLE 1

| Formulation | PLGA RG503[a] (wt %) | PLGA RG502[b] (wt %) | LMW PLGA[c] (wt %) | Benzyl Benzoate (wt %) | Benzyl Alcohol (wt %) |
|---|---|---|---|---|---|
| 1 | 0 | 50 | 0 | 50 | 0 |
| 2 | 7.5 | 24.5 | 18 | 50 | 0 |
| 3 | 10.5 | 0 | 39.5 | 50 | 0 |
| 4 | 0 | 50 | 0 | 25 | 25 |
| 5 | 7.5 | 24.5 | 18 | 25 | 25 |
| 6 | 10.5 | 0 | 39.5 | 25 | 25 |
| 7 | 0 | 50 | 0 | 0 | 50 |
| 8 | 7.5 | 24.5 | 18 | 0 | 50 |
| 9 | 10.5 | 0 | 39.5 | 0 | 50 |
| 10 | 0 | 45 | 0 | 50 | 5 |
| 11 | 6.8 | 22 | 16.2 | 50 | 5 |
| 12 | 9.5 | 0 | 35.5 | 50 | 5 |
| 13 | 0 | 45 | 0 | 41.3 | 13.7 |
| 14 | 6.8 | 22 | 16.2 | 41.3 | 13.7 |
| 15 | 9.5 | 0 | 35.5 | 41.3 | 13.7 |
| 16 | 0 | 45 | 0 | 0 | 55 |
| 17 | 6.8 | 22 | 16.2 | 0 | 55 |
| 18 | 9.5 | 0 | 35.5 | 0 | 55 |
| 19 | 0 | 40 | 0 | 45 | 15 |
| 20 | 6 | 19.6 | 14.4 | 45 | 15 |
| 21 | 8.4 | 0 | 31.6 | 45 | 15 |
| 22[d] | 0 | 45 | 0 | 45 | 0 |
| 23[d] | 9.5 | 0 | 35.5 | 45 | 0 |

[a]High Molecular Weight (HMW) PLGA (RG 503), MW = 38,000;
[b]Medium Molecular Weight (MMW) PLGA RG 502, MW = 16,000;
[c]Low Molecular Weight (LMW) PLGA, MW = 8,000; and
[d]10% drug loading.

Example 2 hGH Particle Preparation

Human growth hormone (hGH) particles (optionally containing zinc acetate) were prepared as follows:

hGH solution (5 mg/ml) solution in water (BresaGen Corporation, Adelaide, Australia) was concentrated to 10 mg/mL using a Concentration/Dialysis Selector diafiltering apparatus. The diafiltered hGH solution was washed with five times volume of tris or phosphate buffer solution (pH 7.6). Particles of hGH were then formed by spray drying or lyophilization using conventional techniques. Phosphate buffer solutions (5 or 50 mM) containing hGH (5 mg/mL) (and optionally various levels of zinc acetate (0 to 30 mM) when Zn complexed particles were prepared) were spray-dried using a Yamato Mini Spray dryer set at the following parameters:

| Spray Dryer Parameter | Setting |
| --- | --- |
| Atomizing Air | 2 psi |
| Inlet Temperature | 120° C. |
| Aspirator Dial | 7.5 |
| Solution Pump | 2-4 |
| Main Air Valve | 40-45 psi | hGH particles having a size range between 2 to 100 microns were obtained. Lyophilized particles were prepared from tris buffer solutions (5 or 50 mM: pH 7.6) containing hGH (5 mg/mL) using a Durastop μP Lyophilizer in accordance with the following freezing and drying cycles:

| | |
| --- | --- |
| Freezing cycle | Ramp down at 2.5 C/min to −30° C. and hold for 30 minutes<br>Ramp down at 2.5 C/min to −30° C. and hold for 30 minutes |
| Drying cycle | Ramp up at 0.5 C/min to 10° C. and hold for 960 minutes<br>Ramp up at 0.5 C/min to 20° C. and hold for 480 minutes<br>Ramp up at 0.5 C/min to 25° C. and hold for 300 minutes<br>Ramp up at 0.5 C/min to 30° C. and hold for 300 minutes<br>Ramp up at 0.5 C/min to 5° C. and hold for 5000 minutes | hGH particles having a size range between 2 to 100 microns were obtained.

Example 3 hGH-Stearic Acid Particle Preparation

Human growth hormone (hGH) particles were prepared as follows: Lyophilized hGH (3.22 grams, Pharmacia-Upjohn, Stockholm, Sweden) and stearic acid (3.22 grams, 95% pure, Sigma-Aldrich Corporation, St. Louis, Mo.) were blended and ground. The ground material was compressed in a 13 mm round die, with a force of 10,000 pounds for five minutes. Compressed tablets were ground and sieved through a 70 mesh screen followed by a 400 mesh screen to obtain particles having a size range between 38 to 212 microns.

Example 4

Bupivacaine Base Preparation

Bupivacaine hydrochloride (Sigma-Aldrich Corporation, St. Louis, Mo.) was dissolved in de-ionized (DI) water at a concentration of 40 mg/ml (saturation). A calculated amount of sodium hydroxide (in the form of 1 N solution) was added to the solution and the pH of the final mixtures was adjusted to ten to precipitate the Bupivacaine base. The precipitated product was filtered, and further washed with DI water for at least three times. The precipitated product was dried at ca. 40° C. in vacuum for 24 hours.

Example 5

Bupivacaine Particle Preparation

Bupivacaine drug particles (both base and hydrochloride salt) were prepared as follows. Bupivacaine hydrochloride (Sigma-Aldrich Corporation, St. Louis, Mo.) or bupivacaine base prepared according Example 4 were ground and then sieved to a fixed range using three inch stainless steel sieves. Typical ranges include 25 μm to 38 μm, 38 μm to 63 μm, and 63 μm to 125 μm.

Example 6

Bupivacaine-Stearic Acid Particle Preparation

Bupivacaine particles were prepared as follows: Bupivacaine hydrochloride (100 grams, Sigma-Aldrich Corporation, St. Louis, Mo.) was ground and sieved through 63 to 125 micron sieves. The bupivacaine particles and stearic acid (100 grams, 95% pure, Sigma-Aldrich Corporation, St. Louis, Mo.) were blended and ground. The ground material was compressed in a 13 mm round die, with a force of 5,000 pounds for five minutes. Compressed tablets were ground and sieved through a 120 mesh screen followed by a 230 mesh screen to obtain particles having a size range between 63 to 125 microns.

Example 7

Drug Loading

Particles comprising beneficial agent with or without stearic acid prepared as above are added to a gel vehicle in an amount of 10 to 30% by weight and blended manually until the dry powder is wetted completely. Then, the milky light yellow particle/gel mixture is thoroughly blended by conventional mixing using a Caframo mechanical stirrer with an attached square-tip metal spatula. Final homogenous depot compositions were transferred to 3, 10 or 30 cc disposable syringes for storage or dispensing.

A representative number of implantable depots were prepared in accordance with the foregoing procedures and tested for in vitro release of beneficial agent as a function of time and also in in vivo studies in rats to determine release of the beneficial agent as determined by blood serum or plasma concentrations of beneficial agent as a function of time.

Example 8

Bupivacaine In Vivo Studies

In vivo studies in rats (four or five per group) were performed following an open protocol to determine plasma levels of bupivacaine upon systemic administration of bupivacaine via the implant systems of this invention. Depot gel bupivacaine compositions were loaded into customized 0.5 cc disposable syringes. Disposable 18-gauge needles were attached to the syringes and were heated to 37° C. using a circulator bath. Depot gel bupivacaine compositions were injected into rats and blood was drawn at specified time intervals (one hour, four hours and on days 1, 2, 5, 7, 9 and 14, 21 and 28) and analyzed for bupivacaine using LC/MS.

Example 9 hGH In Vivo Studies

In vivo hGH studies in rats were performed following an open protocol to determine serum levels of hGH upon systemic administration of hGH via the implant systems of this invention. Depot gel hGH compositions were loaded into customized 0.5 cc disposable syringes. Disposable 16-gauge needles were attached to the syringes and were heated to 37° C. using a circulator bath. Depot gel hGH compositions were injected into immunosuppressed rats and blood was drawn at specified time intervals. All serum samples were stored at 4°

C. prior to analysis. Samples were analyzed for intact hGH content using a radio immuno assay (RIA).

Example 10

Viscosity and Injection Force Measurement of Depot Gel Compositions

Viscosity of the depot vehicle compositions was tested using a Bohlin CVO 120 rheometer. All testing was done at 24° C. using 20 mm parallel plates. The injection force of the depot vehicle compositions was tested on an Instron tensile testing instrument, where the maximum force required to move the syringe plunger at a speed of 1 ml/minute was determined. The vehicle compositions were prefilled into Hamilton syringes prior to the Instron tests. All tests were conducted at room temperature, using a 24-gauge 0.5-inch-long needle.

Example 11

Vehicle Compositions in Benzyl Benzoate

The depot vehicles were formulated with benzyl benzoate as the solvent and the PLGAs with various molecular weight distributions (unimodal, like PLGA RG502, bimodal, like the mixture of HMW PLGA RG503 with LMW PLGA, or multimodal, like the mixture of HMW PLGA RG503, MMW RG502 and LMW PLGA, see Table 1 formulations 1 through 3) having a polymer/solvent ratio of 50/50. As can be seen in FIG. 1, significant shear thinning behavior was found with the vehicle composition having bimodal molecular weight distribution as described in this invention.

Example 12

GPC Measurement on PLGAs with Various Molecular Weight Distributions

Figure 2:
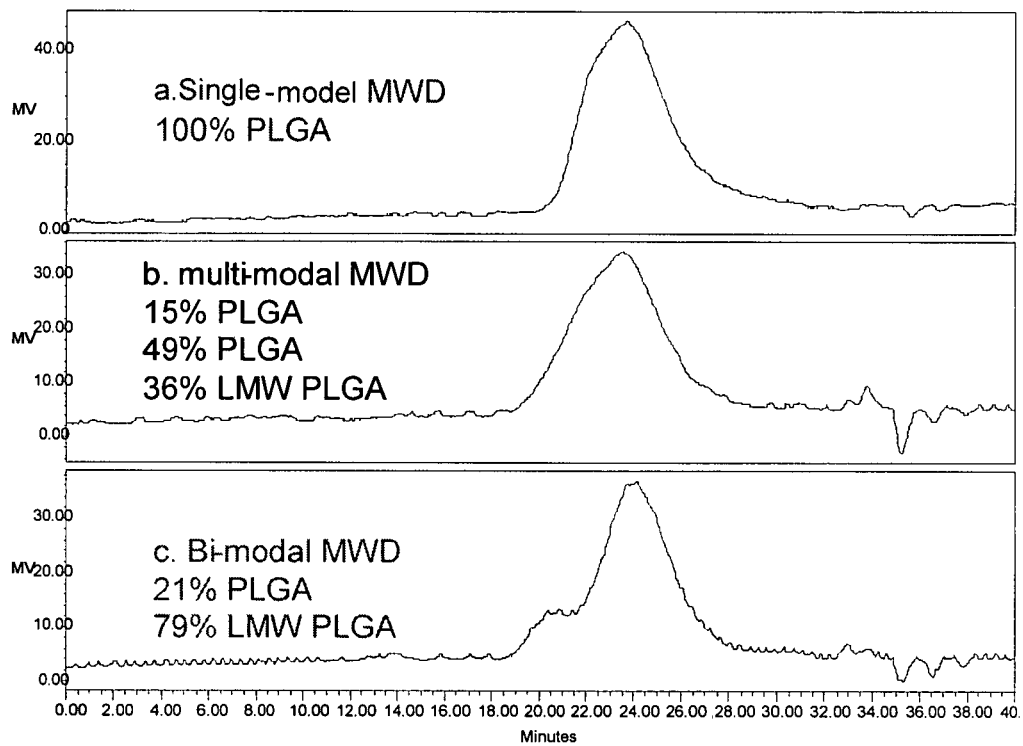
FIG. 2 is a graph illustrating the gel permeation chromatography (GPC) diagrams of PLGA polymers with different molecular weight distribution present in this invention.

The molecular weight and molecular weight distribution of the PLGAs was measured by Gel Permeation Chromatography (GPC) using Waters 600E (Milford, Mass.) equipped with Waters 410 Differential Refractometer detector, THF as solvent with an elution rate of 1 ml/minute. Polystyrene was used as standard. As illustrated in FIG. 2, the three PLGAs used in the Example 11 (formulations 1, 2 and 3) have a $M_w$ of 16,000, but with molecular weight distributions (MWD, $M_w/M_n$) of 1.90, 2.75, and 2.34 for single modal, bimodal and multimodal MWD PLGAs, respectively.

Example 13

Vehicle Compositions in Benzyl Alcohol with Polymer/Solvent Ratio of 50/50

Figure 3:
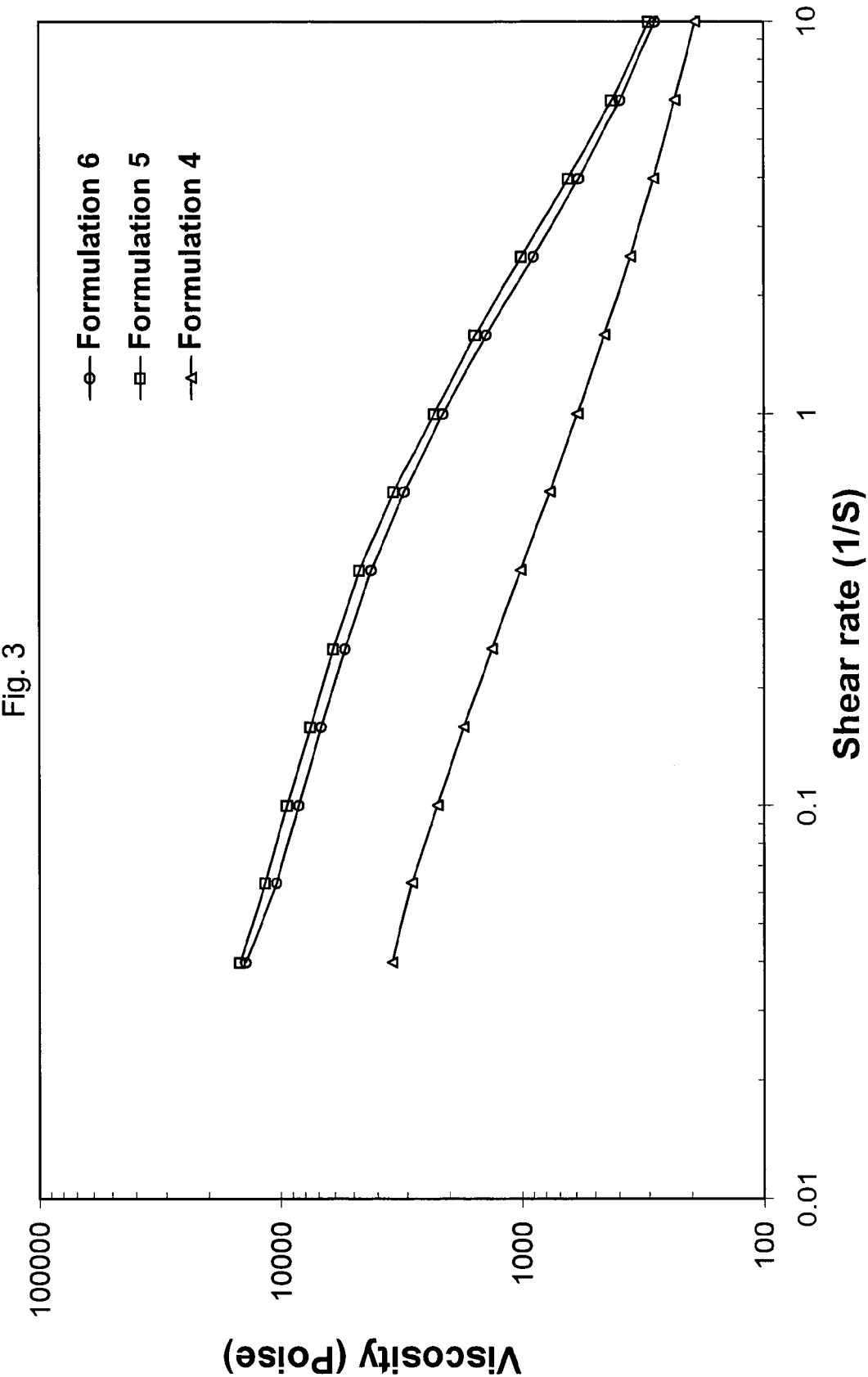
FIG. 3 is a graph illustrating the rheological behavior of depot gel compositions present in this invention (formulations 4 through 6).

The depot vehicles were also formulated with benzyl alcohol as the solvent and the PLGAs having various molecular weight distributions (single modal, like MMW PLGA RG502, bimodal, like the mixture of HMW PLGA RG503 with LMW PLGA, or multimodal, like the mixture of HMW PLGA RG503, MMW RG502 and LMW PLGA, see Table 1 formulations 4 through 6) with a polymer/solvent ratio of 50/50. As can be seen in FIG. 3, significant shear thinning behaviors were found with the vehicle formulations having both bimodal and multimodal molecular weight distribution as described in this invention.

Example 14

Vehicle Compositions in Benzyl Alcohol with Polymer/Solvent Ratio of 45/55

Figure 4:
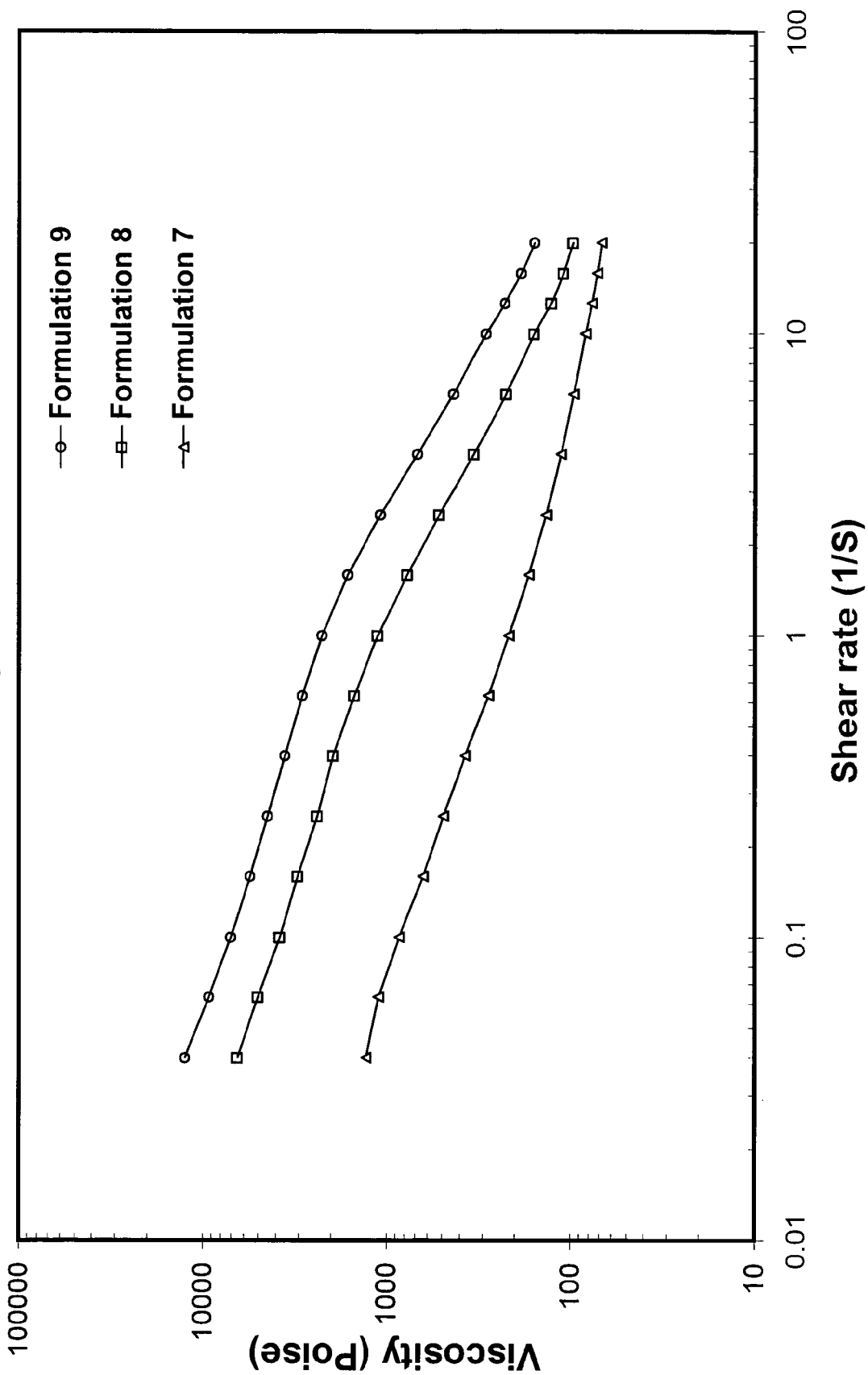
FIG. 4 is a graph illustrating the rheological behavior of depot gel compositions present in this invention (formulations 7 through 9).
Figure 5:
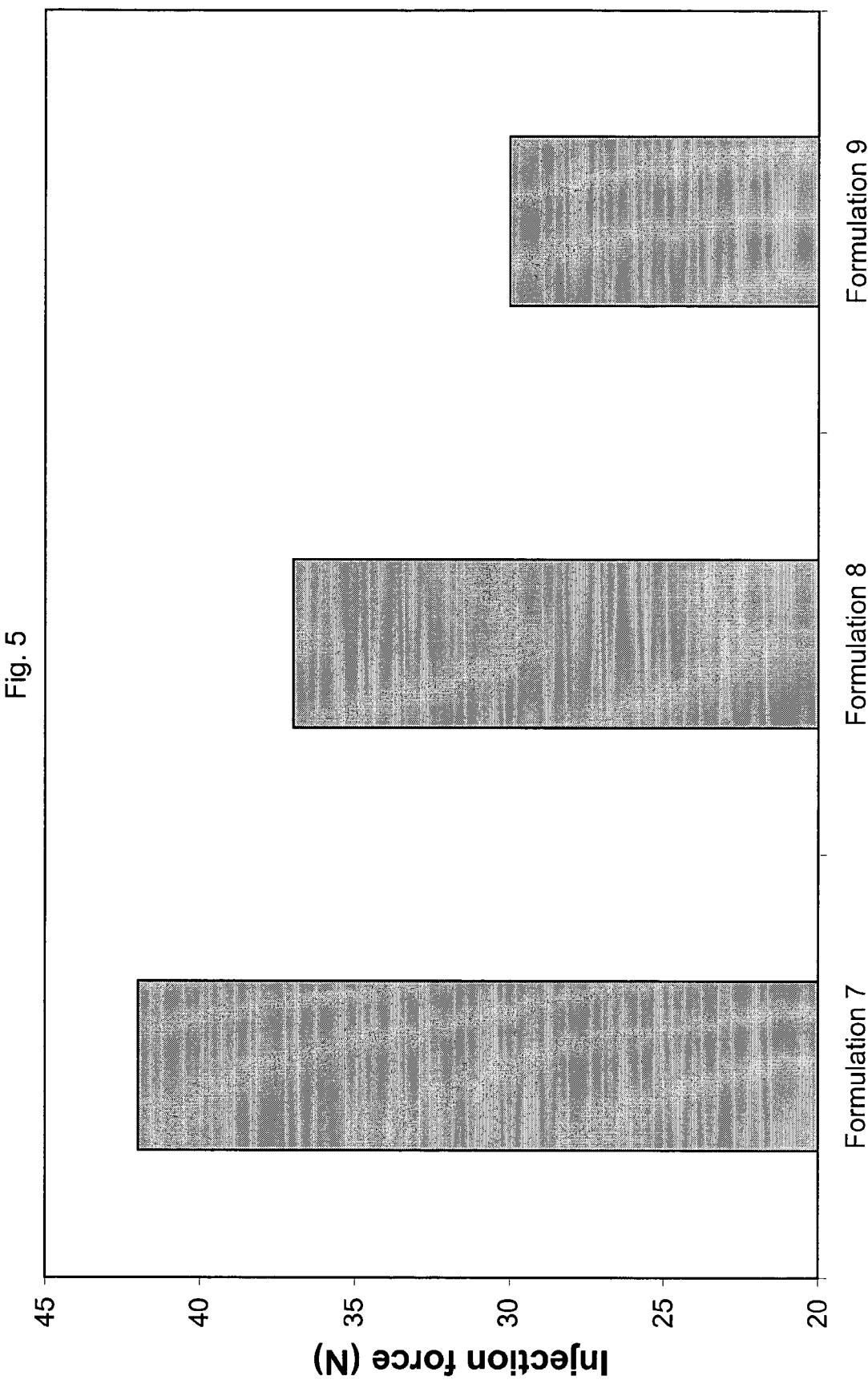
FIG. 5 is a graph illustrating the injection force of depot gel compositions presented in this invention (formulations 7 through 9).

The depot vehicles were formulated with benzyl alcohol as the solvent and the PLGAs with various molecular weight distributions (single modal, like MMW PLGA RG502, bimodal, like mixture of HMW PLGA RG503 with LMW PLGA, or multimodal, like the mixture of HMW PLGA RG503, MMW RG502 and LMW PLGA, see Table 1 formulations 7 through 9) with a polymer/solvent ratio of 45/55. As can be seen in FIGS. 4 and 5, significant shear thinning behaviors and lower injection forces were found with the vehicle compositions having both bimodal and multimodal molecular weight distribution as described in this invention.

Example 15

Vehicle Compositions in the Mixture of Benzyl Benzoate and Benzyl Alcohol (25/25)

Figure 6:
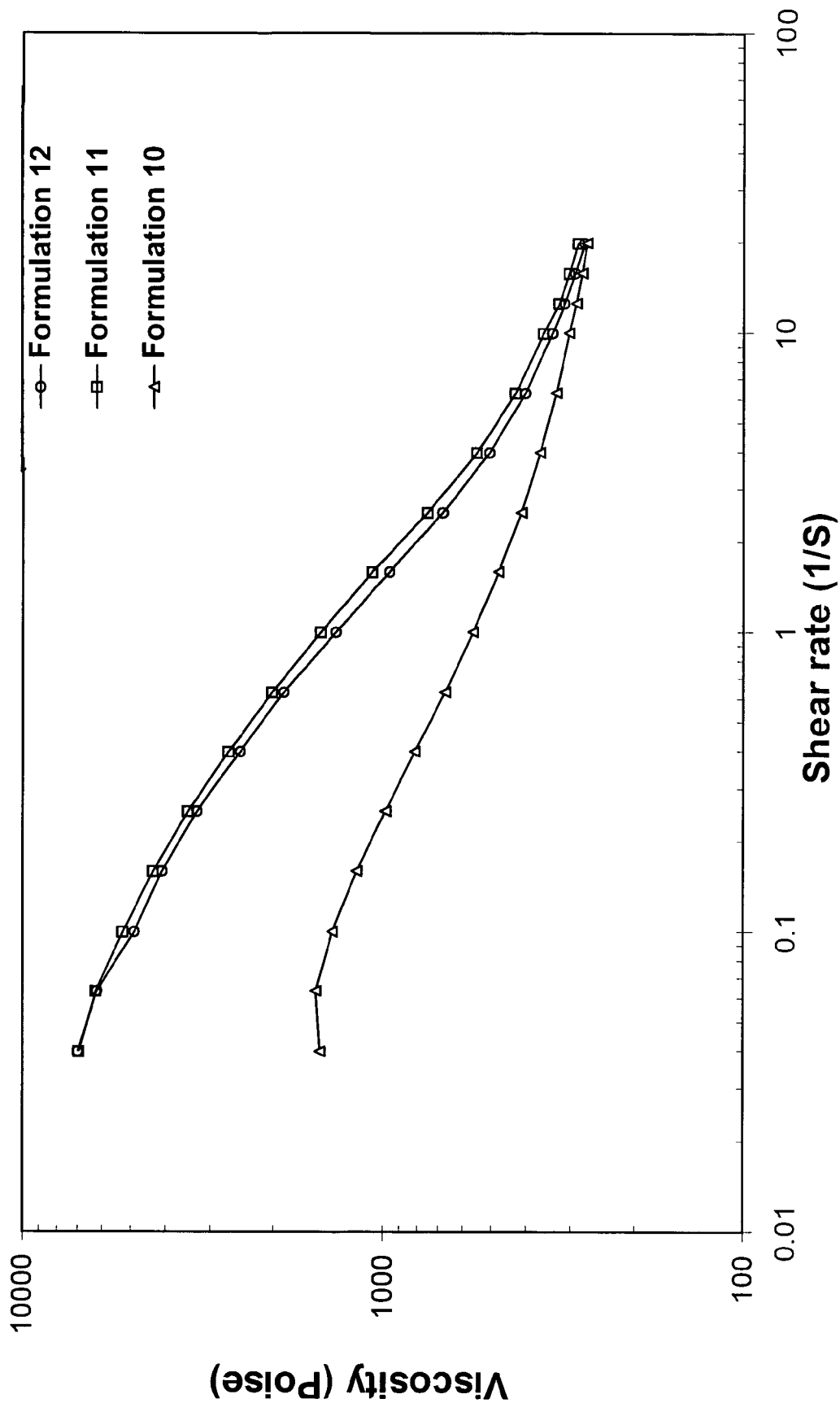
FIG. 6 is a graph illustrating the rheological behavior of depot gel compositions present in this invention (formulations 10 through 12).
Figure 7:
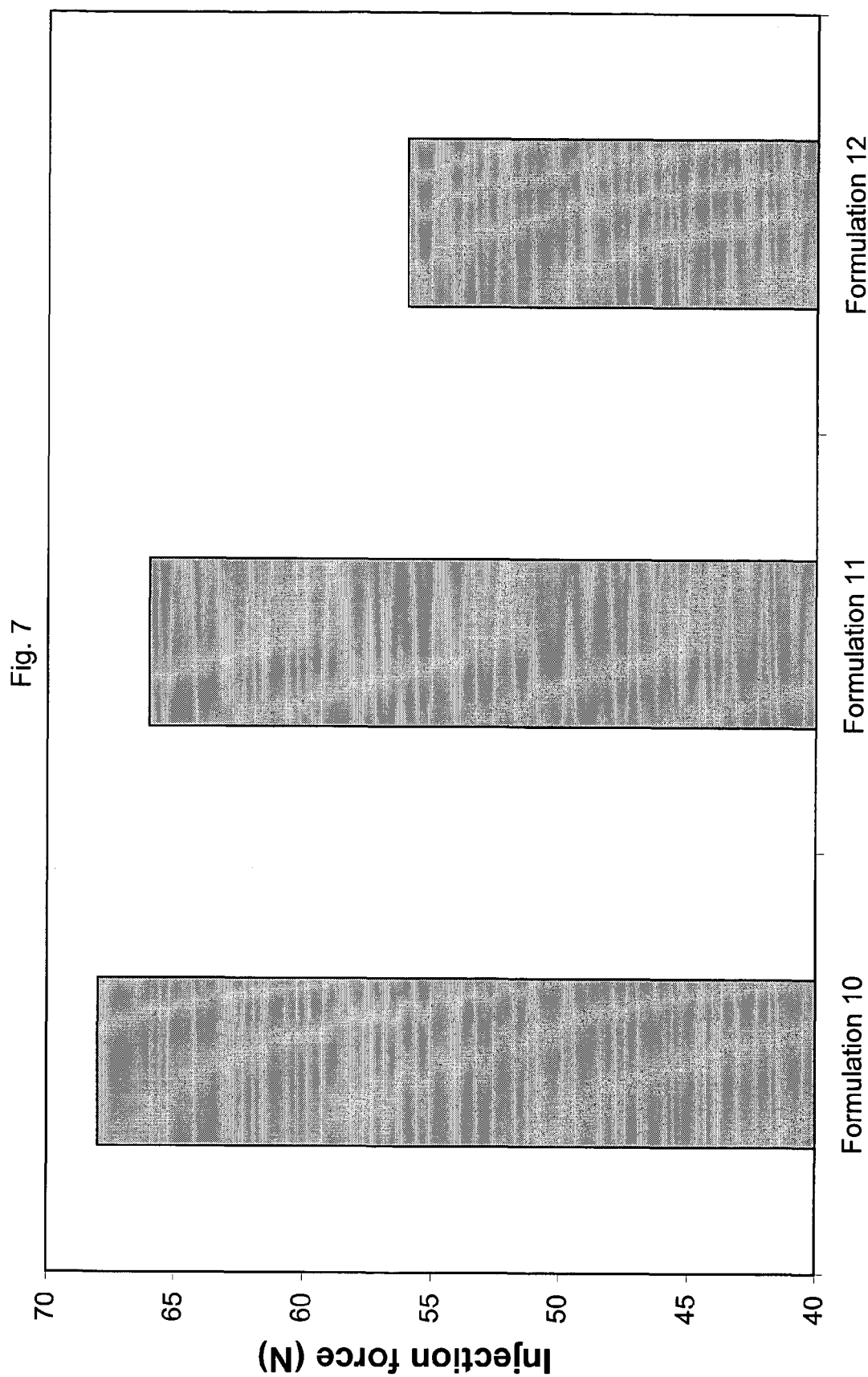
FIG. 7 is a graph illustrating the rheological behavior of depot gel compositions present in this invention (formulations 13 through 15).

The depot vehicles were formulated with the mixtures of benzyl benzoate and benzyl alcohol (50/50) as the solvent and the PLGAs with various molecular weight distributions (single modal, like MMW PLGA RG502, bimodal, like the mixture of HMW PLGA RG503 with LMW PLGA, or multimodal, like the mixture of HMW PLGA RG503, MMW RG502 and LMW PLGA, see Table 1 formulations 10 through 12) with a polymer/solvent ratio of 50/50. As can be seen in FIGS. 6 and 7, significant shear thinning behaviors and lower injection forces were found with the vehicle compositions having both bimodal and multimodal molecular weight distribution as described in this invention.

Example 16

Vehicle Compositions in the Mixture of Benzyl Benzoate and Benzyl Alcohol (41.3/13.7)

Figure 8:
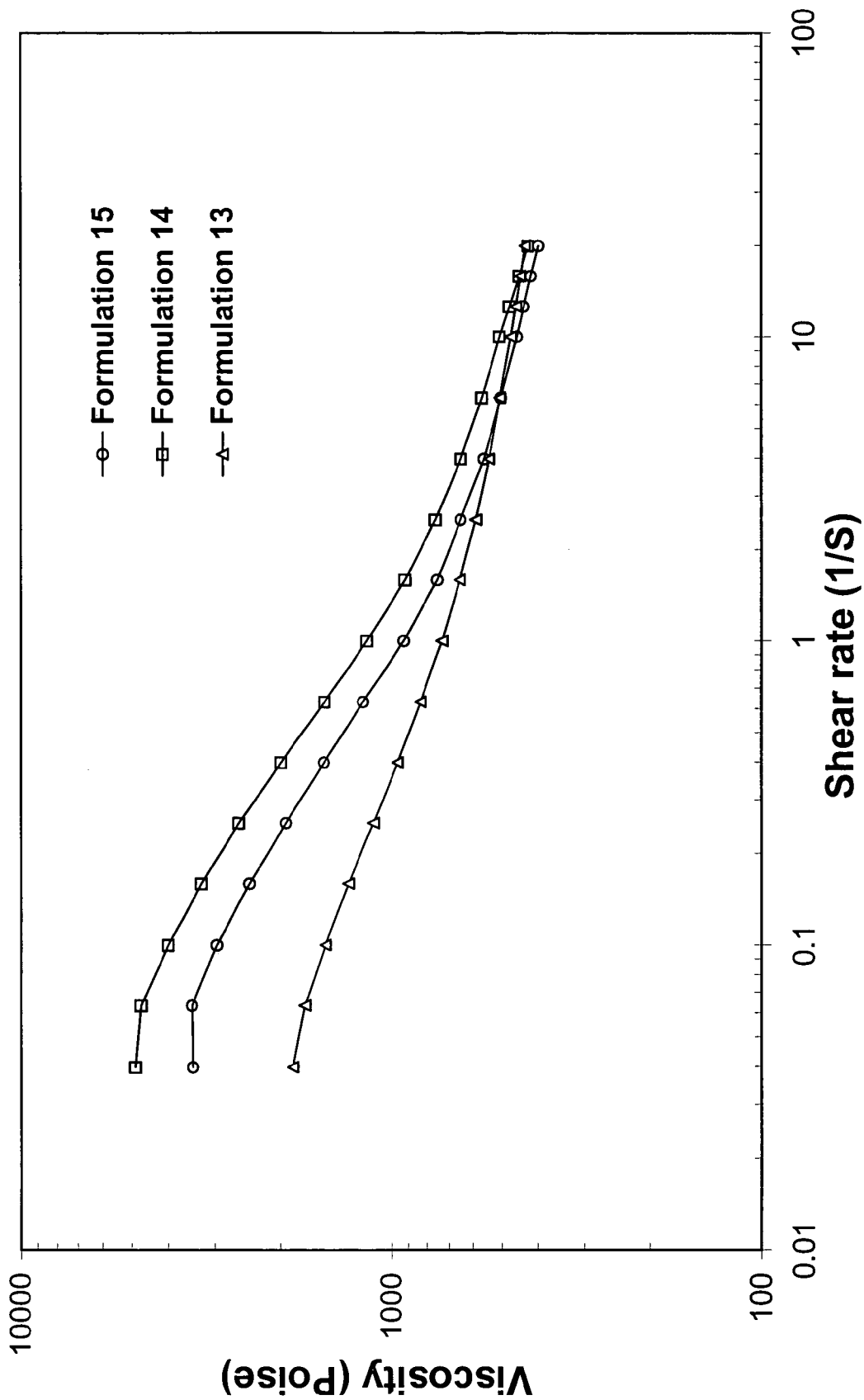
FIG. 8 is a graph illustrating the injection force of depot gel compositions presented in this invention (formulations 13 through 15).

The depot vehicles were formulated with the mixtures of benzyl benzoate and benzyl alcohol (41.3/13.7) as the solvent and the PLGAs with various molecular weight distributions (single modal, like MMW PLGA RG502, bimodal, like the mixture of HMW PLGA RG503 with LMW PLGA, or multimodal, like the mixture of HMW PLGA RG503, MMW RG502 and LMW PLGA, see Table 1 formulations 13 through 15) with a polymer/solvent ratio of 45/55. As can be seen in FIG. 8, significant shear thinning behaviors were found with the vehicle compositions having both bimodal and multimodal molecular weight distribution as described in this invention.

Example 17

Vehicle Compositions in the Mixture of Benzyl Alcohol with Polymer/Solvent Ratio of 45/55

Figure 9:
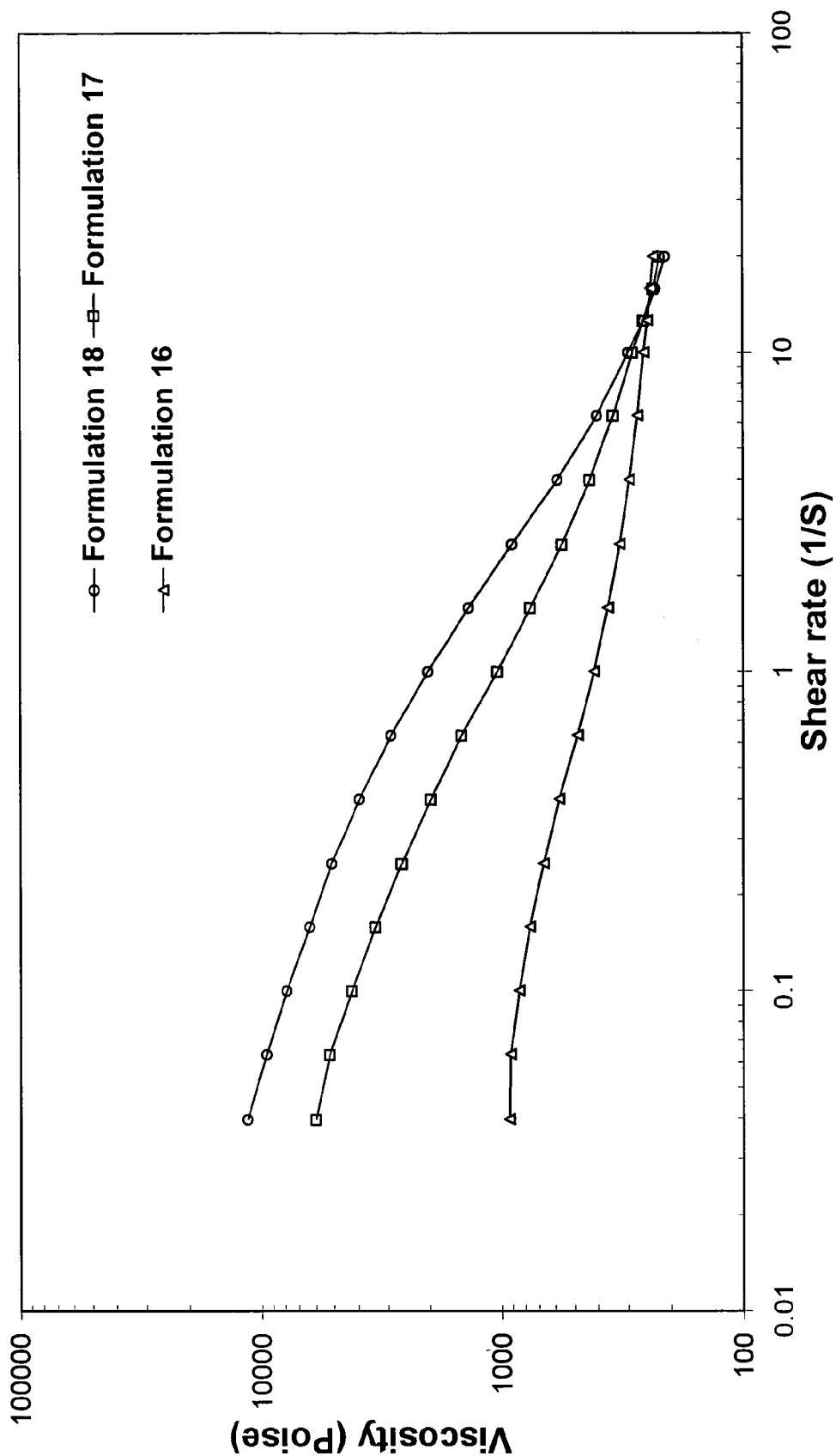
FIG. 9 is a graph illustrating the rheological behavior of depot gel compositions present in this invention (formulations 16 through 18).
Figure 10:
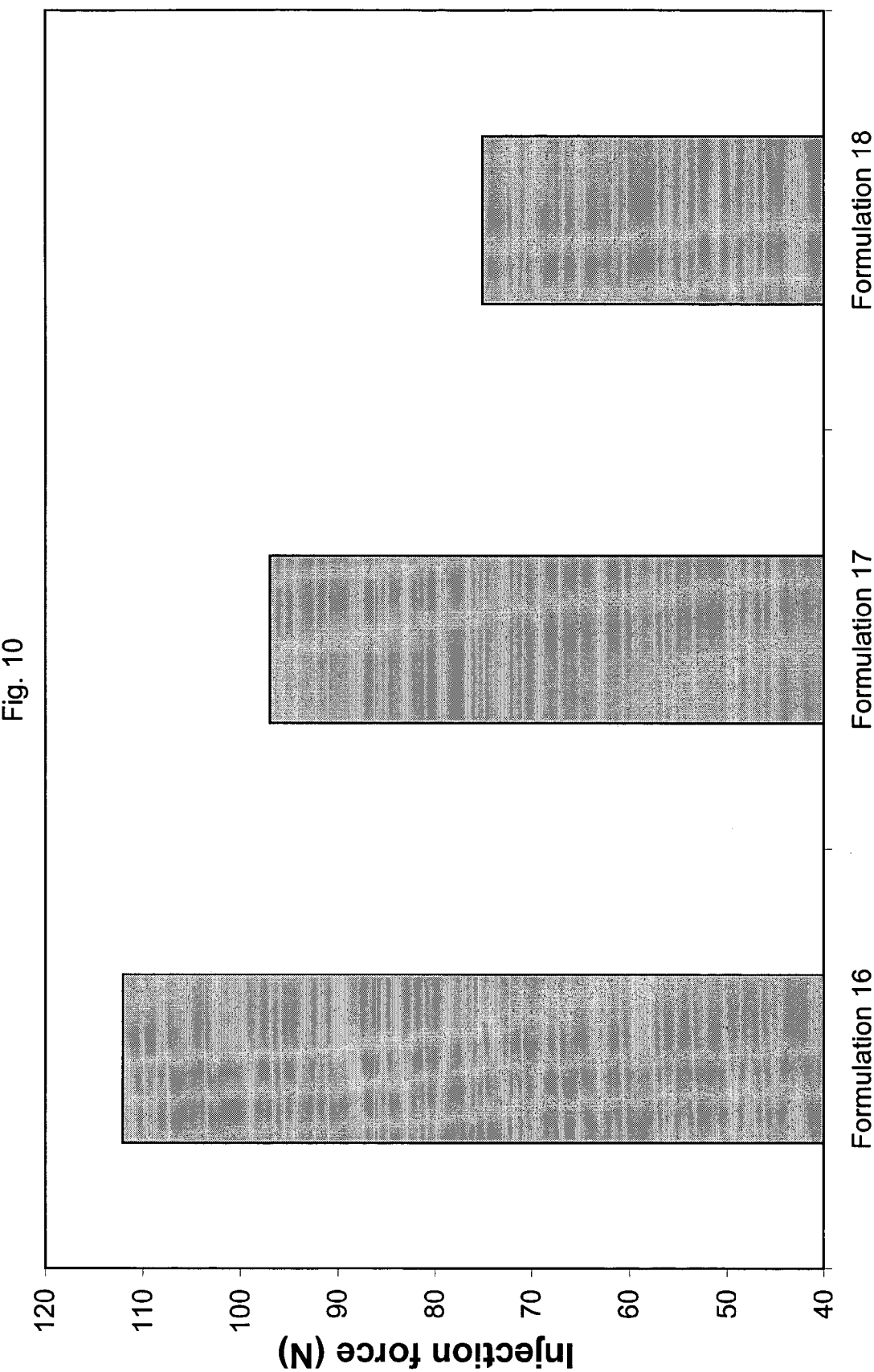
FIG. 10 is a graph illustrating the injection force of depot gel compositions presented in this invention (formulations 16 through 18).

The depot vehicles were formulated with the benzyl alcohol as the solvent and the PLGAs with various molecular weight distributions (single modal, like MMW PLGA RG502, bimodal, like the mixture of HMW PLGA RG503 with LMW PLGA, or multimodal, like the mixture of HMW PLGA RG503, MMW RG502 and LMW PLGA, see Table 1 formulations 16 through 18) with a polymer/solvent ratio of 45/55. As can be seen in FIGS. 9 and 10, significant shear thinning behaviors and lower injection forces were found with the vehicle compositions having both bimodal and multimodal molecular weight distribution as described in this invention.

Example 18

Vehicle Compositions in the Mixture of Benzyl Benzoate and Benzyl Alcohol (45/15) with Polymer/Solvent Ratio of 40/60

Figure 11:
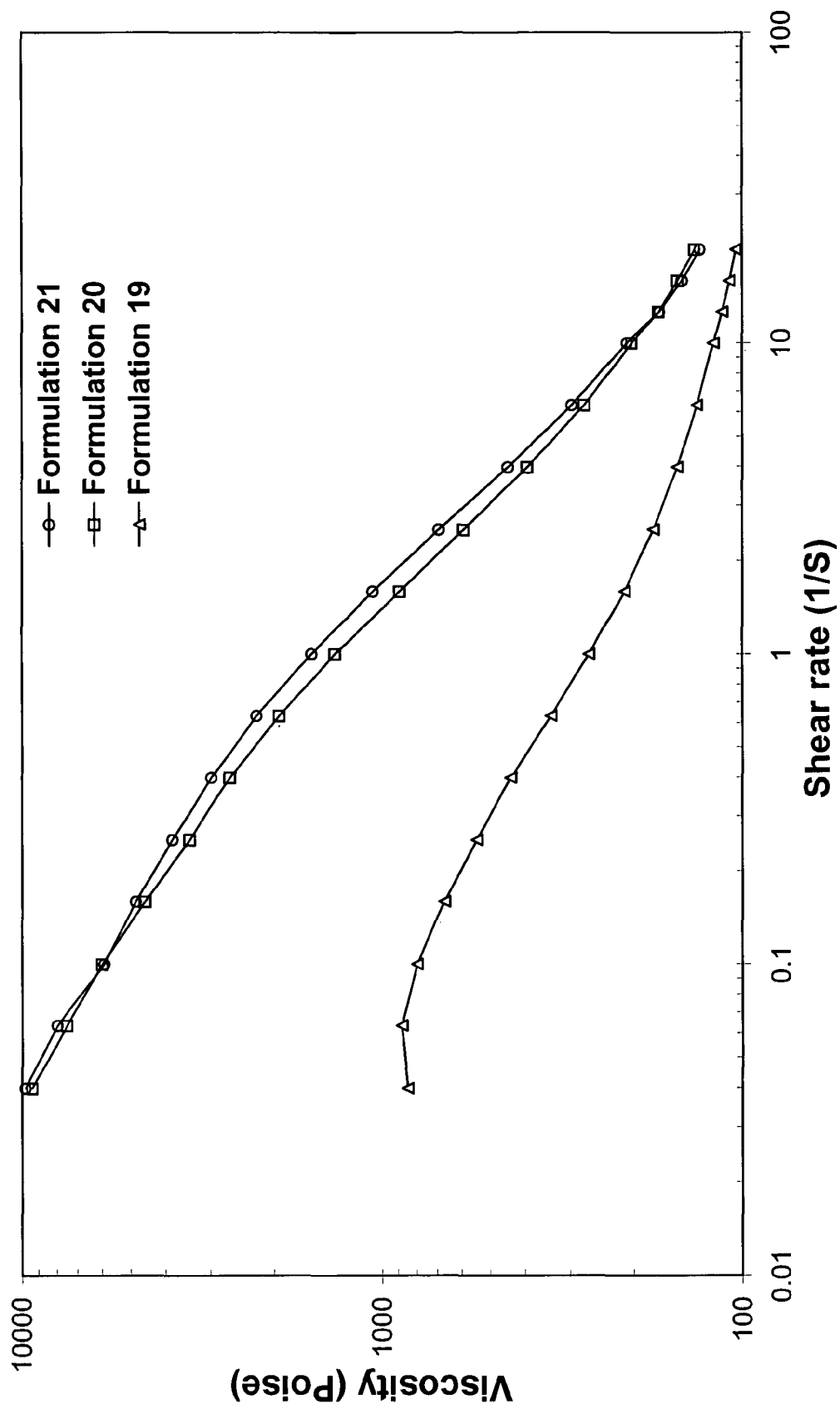
FIG. 11 is a graph illustrating the rheological behavior of depot gel compositions present in this invention (formulations 19 through 21).
Figure 12:
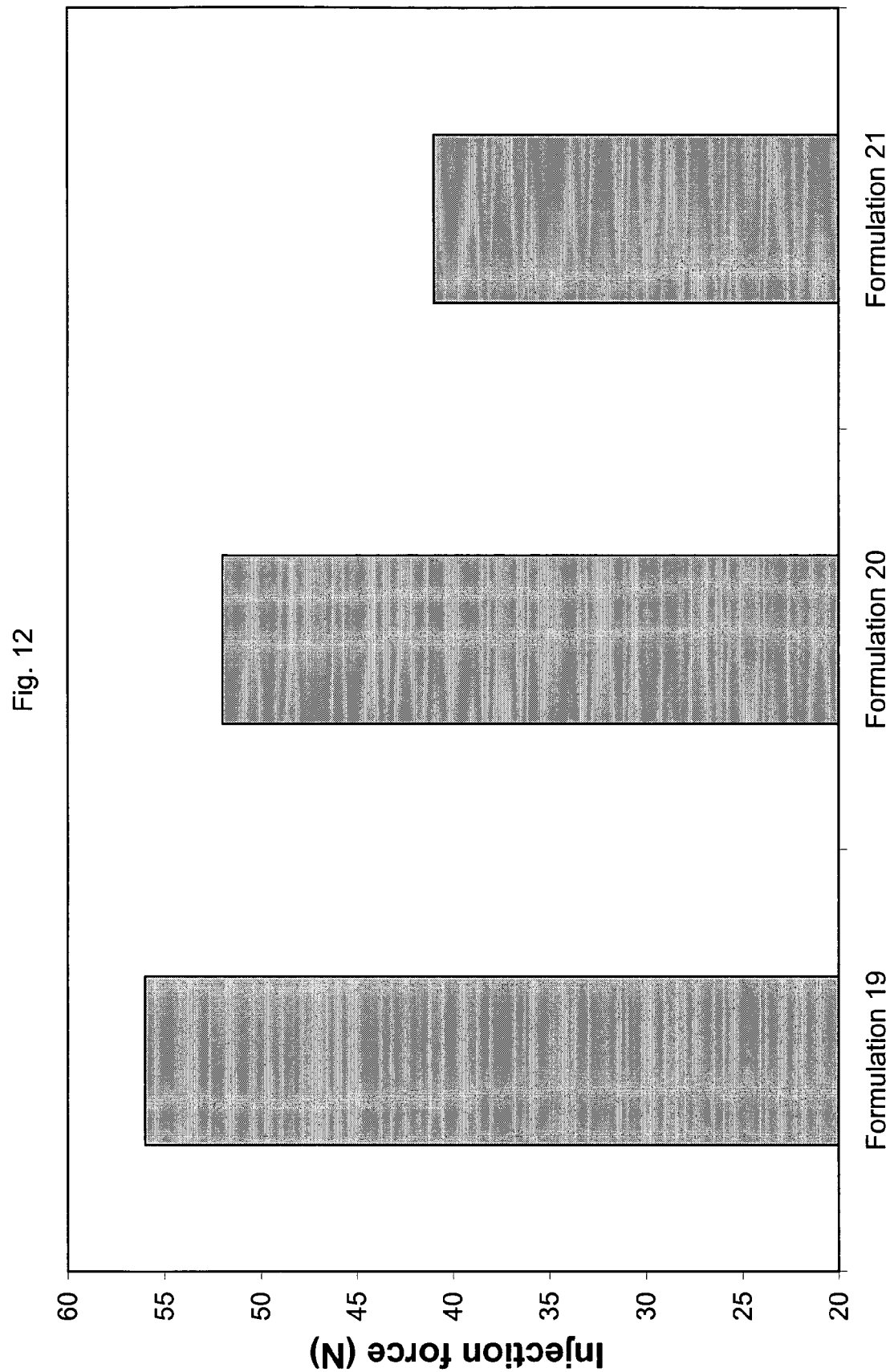
FIG. 12, is a graph illustrating the injection force of depot gel compositions presented in this invention (formulations 19 through 21).

The depot vehicles were formulated with the mixtures of benzyl benzoate and benzyl alcohol (45/15) as the solvent and the PLGAs with various molecular weight distributions (single modal, like MMW PLGA RG502, bimodal, like the mixture of HMW PLGA RG503 with LMW PLGA, or multimodal, like the mixture of HMW PLGA RG503, MMW RG502 and LMW PLGA, see Table 1 formulations 19 through 21) with a polymer/solvent ratio of 40/60. As can be seen in FIGS. 11 and 12, significant shear thinning behaviors and lower injection forces were found with the vehicle compositions having both bimodal and multimodal molecular weight distribution as described in this invention.

Example 19

In Vivo Studies on Bupivacaine Depot Composition with Different PLGA Molecular Weight Distributions As illustrated in Table 1, various depot vehicle compositions can be made from the PLGAs with different molecular weight distribution in different solvents, such as benzyl benzoate, benzyl alcohol, and mixtures thereof, with different polymer/solvent ratios. The depot compositions can be made with loaded drug particles either with or without hydrophobic excipients, such as stearic acid (SA) into depot vehicles as described in this invention.

As illustrated in Table 1, the bupivacaine depots were formulated with the PLGAs with two different molecular weight distributions in benzyl benzoate (single modal, like MMW PLGA RG502, HMW bimodal, like the mixture of PLGA RG503 with LMW PLGA, Table 1 formulations 22 and 23). FIG. 13 illustrates the representative in vivo release profiles of bupivacaine obtained in rats from the formulations 22 and 23.

As illustrated in this example, the depot composition using the PLGA with the bimodal molecular weight distribution showed the similar release rate profile to the one with the single molecular weight distribution, but with more significant shear thinning behavior and lower injection force.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention.

We claim:

1. An injectable depot composition comprising:
   (a) a polymer matrix comprising a plurality of bioerodible, biocompatible lactic acid-based polymers, wherein a first of said plurality of polymers is a low molecular weight (LMW) polymer having a weight average molecular weight ranging from about 3000 to about 10,000 and a second is a high molecular weight (HMW) polymer having a weight average molecular weight of greater than about 30,000, the polymer matrix having a bimodal molecular weight distribution of the plurality of polymers;
   (b) a solvent having a miscibility in water of less than or equal to 7% at 25° C., in an amount effective to plasticize the plurality of polymers and form a gel therewith, wherein the solvent is a solvent selected from the group consisting of aromatic alcohols, esters of aromatic acids, aromatic ketones, and mixtures thereof; and
   (c) a beneficial agent dissolved or dispersed in the gel.

2. An injectable depot composition comprising:
   (a) a polymer matrix comprising a plurality of bioerodible, biocompatible lactic acid-based polymers, wherein a first of said plurality of polymers is a low molecular weight (LMW) polymer having a weight average molecular weight ranging from about 3000 to about 9000, a second is a high molecular weight (HMW) polymer having a weight average molecular weight greater than 30,000, and a third is a medium molecular weight (MMW) polymer having a weight average molecular weight ranging from 10,000 to 30,000, the polymer matrix having a multimodal molecular weight distribution of the plurality of polymers;
   (b) a solvent having a miscibility in water of less than or equal to 7% at 25° C., in an amount effective to plasticize the plurality of polymers and form a gel therewith, wherein the solvent is a solvent selected from the group consisting of aromatic alcohols, esters of aromatic acids, aromatic ketones, and mixtures thereof; and
   (c) a beneficial agent dissolved or dispersed in the gel.

3. The injectable depot composition of claim 1, wherein the polymer matrix comprises about 20 wt % to about 90 wt % of the low molecular weight (LMW) polymer.

4. The composition of claim 1, wherein each polymer is a copolymer of lactic acid and glycolic acid.

5. The composition of claim 1, comprising about 5 wt % to about 90 wt % of the biodegradable, biocompatible lactic acid-based polymers.

6. The composition of claim 5, comprising about 25 wt % to about 80 wt % of the biodegradable, biocompatible lactic acid-based polymers.

7. The composition of claim 1, wherein the solvent has a miscibility in water of less than or equal to 5 wt % at 25° C.

8. The composition of claim 7, wherein the solvent has a miscibility in water of less than or equal to 3 wt % at 25° C.

9. The composition of claim 8, wherein the solvent has a miscibility in water of less than or equal to 1 wt % at 25° C.

10. The composition of claim 9, wherein the solvent has a miscibility in water of less than or equal to 0.5 wt % at 25° C.

11. The injectable depot composition of claim 1, wherein the solvent is an aromatic alcohol that has the structural formula (I)

$$Ar-(L)_n-OH \qquad (I)$$

in which Ar is a substituted or unsubstituted aryl or heteroaryl group, n is zero or 1, and L is a linking moiety.

12. The composition of claim 11, wherein Ar is monocyclic aryl or heteroaryl, n is 1, and L is lower alkylene optionally containing at least one heteroatom.

13. The composition of claim 12, wherein Ar is monocyclic aryl and L is lower alkylene.

14. The composition of claim 13, wherein Ar is phenyl and L is methylene.

15. The composition of claim 1, wherein the ester of an aromatic acid is a lower alkyl ester or an aralkyl ester of benzoic acid.

16. The composition of claim 15, wherein the ester of an aromatic acid is benzyl benzoate and the lower alkyl ester of an aromatic acid is ethyl benzoate.

17. The composition of claim 1, wherein the solvent is a mixture of an aromatic alcohol and an ester of an aromatic acid.

18. The composition of claim 17, wherein the ratio of the aromatic alcohol to the ester of the aromatic acid is in the range of about 1% to about 99% by weight.

19. The composition of claim 18, wherein the ratio of the aromatic alcohol to the ester of the aromatic acid is in the range of about 10% to about 90% by weight.

20. The composition of claim 19, wherein the ratio of the aromatic alcohol to the ester of the aromatic acid is in the range of about 20% to about 80% by weight.

21. An injectable depot composition for systemic delivery of a beneficial agent to a subject in a controlled manner comprising:
  (a) a polymer matrix comprising a plurality of bioerodible, biocompatible lactic acid-based polymers, wherein a first of said plurality of polymers is a low molecular weight (LMW) polymer having a weight average molecular weight ranging from about 3000 to about 9000, a second is a high molecular weight (HMW) polymer having a weight average molecular weight greater than 30,000, and a third is a medium molecular weight (MMW) polymer having a weight average molecular weight ranging from 10,000 to 30,000, the polymer matrix having a multimodal molecular weight distribution of the plurality of polymers;
  (b) a solvent having a miscibility in water of less than or equal to 7% at 25° C., in an amount effective to plasticize the plurality of polymers and form a gel therewith, wherein the solvent is a solvent selected from the group consisting of aromatic alcohols, esters of aromatic acids, aromatic ketones, and mixtures thereof; and
  (c) a beneficial agent dissolved or dispersed in the gel.

22. An injectable depot composition for sustained delivery of a beneficial agent to a subject comprising:
  (a) a polymer matrix comprising a plurality of bioerodible, biocompatible lactic acid-based polymers, wherein a first of said plurality of polymers is a low molecular weight (LMW) polymer having a weight average molecular weight ranging from about 3000 to about 9000, a second is a high molecular weight (HMW) polymer having a weight average molecular weight greater than 30,000, and a third is a medium molecular weight (MMW) polymer having a weight average molecular weight ranging from 10,000 to 30,000, the polymer matrix having a multimodal molecular weight distribution of the plurality of polymers;
  (b) a solvent having a miscibility in water of less than or equal to 7% at 25° C., in an amount effective to plasticize the plurality of polymers and form a gel therewith, wherein the solvent is a solvent selected from the group consisting of aromatic alcohols, esters of aromatic acids, aromatic ketones, and mixtures thereof; and
  (c) a beneficial agent dissolved or dispersed in the gel, wherein the beneficial agent is delivered systemically in a controlled manner over a duration of one year.

23. An injectable depot composition for local delivery of a beneficial agent to a subject in a controlled manner comprising:
  (a) a polymer matrix comprising a plurality of bioerodible, biocompatible lactic acid-based polymers, wherein a first of said plurality of polymers is a low molecular weight (LMW) polymer having a weight average molecular weight ranging from about 3000 to about 9000, a second is a high molecular weight (HMW) polymer having a weight average molecular weight greater than 30,000, and a third is a medium molecular weight (MMW) polymer having a weight average molecular weight ranging from 10,000 to 30,000, the polymer matrix having a multimodal molecular weight distribution of the plurality of polymers;
  (b) a solvent having a miscibility in water of less than or equal to 7% at 25° C., in an amount effective to plasticize the plurality of polymers and form a gel therewith, wherein the solvent is a solvent selected from the group consisting of aromatic alcohols, esters of aromatic acids, aromatic ketones, and mixtures thereof; and
  (c) a beneficial agent dissolved or dispersed in the gel.

24. An injectable depot composition for sustained delivery of a beneficial agent to a subject comprising:
  (a) a polymer matrix comprising a plurality of bioerodible, biocompatible lactic acid-based polymers, wherein a first of said plurality of polymers is a low molecular weight (LMW) polymer having a weight average molecular weight ranging from about 3000 to about 9000, a second is a high molecular weight (HMW) polymer having a weight average molecular weight greater than 30,000, and a third is a medium molecular weight (MMW) polymer having a weight average molecular weight ranging from 10,000 to 30,000, the polymer matrix having a multimodal molecular weight distribution of the plurality of polymers;
  (b) a solvent having a miscibility in water of less than or equal to 7% at 25° C., in an amount effective to plasticize the plurality of polymers and form a gel therewith, wherein the solvent is a solvent selected from the group consisting of aromatic alcohols, esters of aromatic acids, aromatic ketones, and mixtures thereof; and
  (c) a beneficial agent dissolved or dispersed in the gel, wherein the beneficial agent is delivered locally in a controlled manner over a duration of up to one year.

25. The injectable depot composition of any one of claims 21, 22, 23 or 24, wherein the solvent is an aromatic alcohol.

26. The injectable depot composition of claim 25, wherein the polymer matrix comprises about 20 wt % to about 90 wt % of the low molecular weight (LMW) polymer.

27. The composition of claim 24, wherein each polymer is a copolymer of lactic acid and glycolic acid.

28. The composition of claim 24, comprising about 5 wt % to about 90 wt % of the biodegradable, biocompatible lactic acid-based polymers.

29. The composition of claim 28, comprising about 25 wt % to about 80 wt % of the biodegradable, biocompatible lactic acid-based polymers.

30. The composition of claim 25, wherein the solvent has a miscibility in water of less than or equal to 5 wt % at 25° C.

31. The composition of claim 30, wherein the solvent has a miscibility in water of less than or equal to 3 wt % at 25° C.

32. The composition of claim 31, wherein the solvent has a miscibility in water of less than or equal to 1 wt % at 25° C.

33. The composition of claim 32, wherein the solvent has a miscibility in water of less than or equal to 0.5 wt % at 25° C.

34. The injectable depot composition of claim 25, wherein the aromatic alcohol has the structural formula (I)

$$Ar\text{-}(L)_n\text{-}OH \qquad (I)$$

in which Ar is a substituted or unsubstituted aryl or heteroaryl group, n is zero or 1, and L is a linking moiety.

35. The composition of claim 34, wherein Ar is monocyclic aryl or heteroaryl, n is 1, and L is lower alkylene optionally containing at least one heteroatom.

36. The composition of claim 35, wherein Ar is monocyclic aryl and L is lower alkylene.

37. The composition of claim 36, wherein Ar is phenyl and L is methylene.

38. The composition of claim 25, wherein the ester of the aromatic acid is a lower alkyl ester or an aralkyl ester of benzoic acid.

39. The composition of claim 38, wherein the ester of the aromatic acid is benzyl benzoate and the lower alkyl ester of an aromatic acid is ethyl benzoate.

40. The composition of claim 25, wherein the solvent is a mixture of the aromatic alcohol and the ester of the aromatic acid.

41. The composition of claim 40, wherein a ratio of the aromatic alcohol to the ester of the aromatic acid is in the range of about 1% to about 99% by weight.

42. The composition of claim 41, wherein the ratio of the aromatic alcohol to the ester of the aromatic acid is in the range of about 10% to about 90% by weight.

43. The composition of claim 42, wherein the ratio of the aromatic alcohol to the ester of the aromatic acid is in the range of about 20% to about 80% by weight.

44. A kit for administration of a beneficial agent to a subject comprising:
(a) a polymer matrix comprising a plurality of bioerodible, biocompatible lactic acid-based polymers, wherein a first of said plurality of polymers is a low molecular weight (LMW) polymer having a weight average molecular weight ranging from about 3000 to about 9000, a second is a high molecular weight (HMW) polymer having a weight average molecular weight greater than 30,000, and a third is a medium molecular weight (MMW) polymer having a weight average molecular weight ranging from 10,000 to 30,000, the polymer matrix having a multimodal molecular weight distribution of the plurality of polymers;
(b) a solvent having a miscibility in water of less than or equal to 7% at 25° C., in an amount effective to plasticize the plurality of polymers and form a gel therewith, wherein the solvent is a solvent selected from the group consisting of aromatic alcohols, esters of aromatic acids, aromatic ketones, and mixtures thereof;
(c) a beneficial agent dissolved or dispersed in the gel; and optionally, one or more of the following:
(d) an emulsifying agent;
(e) a pore former;
(f) a solubility modulator for the beneficial agent, optionally associated with the beneficial agent; and
(g) an osmotic agent, wherein at least the beneficial agent, optionally associated with the solubility modulator, is maintained separated from the solvent until a time of administration of the beneficial agent to a subject.

* * * * *